United States Patent
Ghovanloo et al.

(10) Patent No.: US 8,958,868 B2
(45) Date of Patent: Feb. 17, 2015

(54) SYSTEMS AND METHODS FOR MULTICHANNEL WIRELESS IMPLANTABLE NEURAL RECORDING

(75) Inventors: Maysam Ghovanloo, Atlanta, GA (US); Ming Yin, Raleigh, NC (US)

(73) Assignees: Georgia Tech Research Corporation, Atlanta, GA (US); North Carolina University, Raleigh, NC (US)

( * ) Notice: Subject to any disclaimer, the term of this patent is extended or adjusted under 35 U.S.C. 154(b) by 1216 days.

(21) Appl. No.: 12/468,015

(22) Filed: May 18, 2009

(65) Prior Publication Data

US 2010/0106041 A1     Apr. 29, 2010

Related U.S. Application Data

(60) Provisional application No. 61/108,888, filed on Oct. 28, 2008.

(51) Int. Cl.
*A61B 5/02* (2006.01)
*A61B 5/00* (2006.01)

(52) U.S. Cl.
CPC ............. *A61B 5/0031* (2013.01); *A61B 5/0006* (2013.01)
USPC ........................................ 600/544

(58) Field of Classification Search
USPC ................................ 600/544–545
See application file for complete search history.

(56) References Cited

U.S. PATENT DOCUMENTS

| | | | |
|---|---|---|---|
| 4,619,265 A * | 10/1986 | Morgan et al. ................... 607/6 |
| 5,222,503 A | 6/1993 | Ives et al. |
| 6,360,122 B1 | 3/2002 | Fischell et al. |
| 6,996,435 B2 | 2/2006 | Baru Fassio |
| 7,187,968 B2 | 3/2007 | Wolf et al. |
| 7,346,312 B2 | 3/2008 | Irazoqui-Pastor et al. |
| 2002/0045920 A1 | 4/2002 | Thompson |
| 2002/0071484 A1 * | 6/2002 | Spichale ....................... 375/238 |
| 2003/0134545 A1 * | 7/2003 | McAdams et al. ............ 439/909 |
| 2004/0127803 A1 | 7/2004 | Berkes et al. |
| 2006/0173364 A1 | 8/2006 | Clancy et al. |
| 2006/0293578 A1 | 12/2006 | Rennaker, II |
| 2007/0213629 A1 | 9/2007 | Greene |

FOREIGN PATENT DOCUMENTS

WO     WO 00/25668     5/2000

OTHER PUBLICATIONS

"Using Pulse Width Modulation for Wireless Transmission of Neural Signals in a Multichannel Neural Recording System" by Ming Yin and Maysam Ghovanloo, Electrical and Computer Engineering Department, North Carolina State University, Raleigh, NC, USA.*

(Continued)

*Primary Examiner* — Patricia Mallari
*Assistant Examiner* — Vasuda Ramachandran
(74) *Attorney, Agent, or Firm* — Troutman Sanders LLP; Ryan A. Schneider; Dustin B. Weeks

(57) ABSTRACT

A system for transmitting bioelectrical signals. The system includes an implantable bioelectrical sensor for receiving at least one bioelectrical signal; an analog-to-time converter for converting the received bioelectrical signal from an analog domain to a time domain signal; and a radio frequency (RF) modulator for transmitting the time domain signal. The the analog-to-time converter and the RF modulator are implantable in a living being.

9 Claims, 27 Drawing Sheets

(56) References Cited

OTHER PUBLICATIONS

"A 15-Channel Wireless Neural Recording System Based on Time Division Multiplexing of Pulse Width Modulated Signals" by Yin et al., Proceedings of 2006 International Conference on Microtechnologies in Medicine and Biology, Okinawa, Japan 9-12, 2006.*

"A Fully-Integrated Mixed Signal Neural Processor for Implantable Multi-Channel Cortical Recording" by A. M. Sodagar et al., IEEE, 2006.*

"An ultra-low power neural recording system using pulse representations" by Du Chen, A dissertation preseneted to the graduate school of the University of Florida, 2006.*

Lazar et al. ["Perfect Recovery and Sensitivity Analysis of Time Encoded Bandlimited Signals" by Lazar et al., IEEE Transactions on Circuits and Systems—I: Regular Papers, vol. 51, No. 10, Oct. 2004].*

* cited by examiner

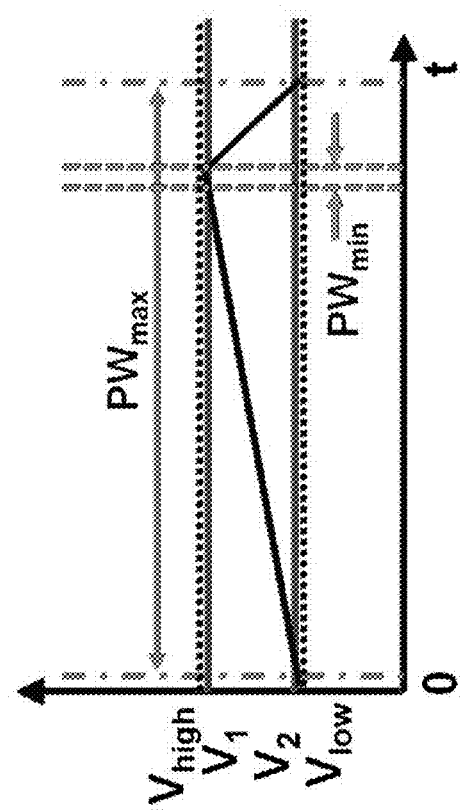
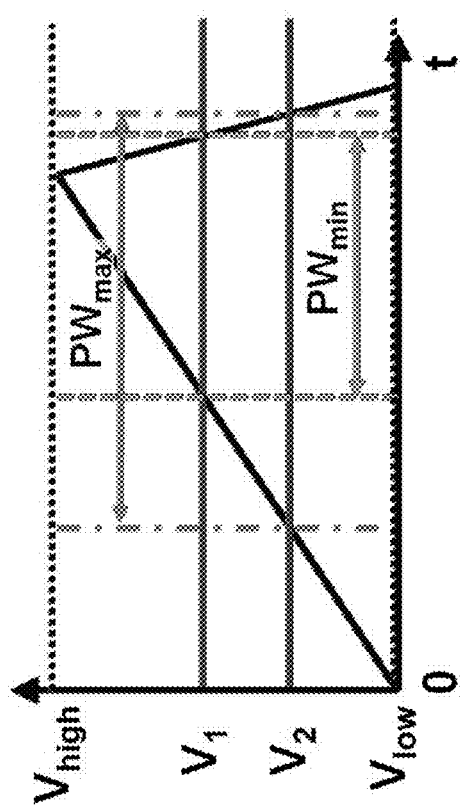
Fig. 7A
Fig. 7B

SYSTEMS AND METHODS FOR MULTICHANNEL WIRELESS IMPLANTABLE NEURAL RECORDING

CROSS REFERENCE TO RELATED APPLICATIONS

This application claims benefit, under 35 U.S.C. §119(e), of U.S. Provisional Application Ser. No. 61/108,888, filed 28 Oct. 2008, the entire contents and substance of which are hereby incorporated by reference.

STATEMENT REGARDING FEDERALLY SPONSORED RESEARCH OR DEVELOPMENT

This invention was made with government support under grant ECCS-824199, awarded by the National Science Foundation (NSF). The federal government has certain rights in the invention.

BACKGROUND

Embodiments of the present invention relate to neural monitoring and, more particularly, to an implantable wireless neural recording system.

Current research in electrophysiology and behavioral neuroscience strives to form a better understanding of the underlying principles of the brain of an animal or a human, and root causes of malfunction in its neuronal circuits. Ongoing research conducted on animal/human models demands systems that can simultaneously record neural signals from a large number of electrodes in awake, behaving animals/humans.

For decades, researchers have used racks of bulky data acquisition systems, connected to electrodes through a bundle of thin wires and a pre-amplifier headstage. This wired solution provides a wide bandwidth and is generally easy to use. Unfortunately, the wires can potentially affect the animal/human behavior by causing psychophysical tethering effects, and adding noise and motion artifacts to the recorded neural signals. To facilitate animal/human mobility and eliminate tangling and twisting of the wires, often a motorized commutator is used on top of the enclosure between the headstage and other instruments. A commutator is a delicate mechanical component and oftentimes the most expensive item in the system. The commutator is also the bottleneck for achieving large channel counts in hardwired setups, and limits experiments to only one animal/human at a time due to twisting and tangling of the wires. Accordingly, providing a natural and enriched environment for animal/human subjects in a hardwired setup is not feasible, either with or without a commutator. Consequently, neuroscientists are interested in replacing the wire bundles with a wireless link and continue recording and processing the "entire" neural signals in their high performance computing clusters without losing any information.

But thus far ongoing neural interfacing research is focused on transferring a limited processing capability to the implantable front-end to limit the required wireless bandwidth at the cost of losing valuable neural information and complicating the implantable unit. Such solutions typically consist of at least a transmitter and a receiver unit before digital signal processing. The transmitter is implanted inside or carried by the animal/human body. It is also responsible for conditioning (mainly amplification and filtering) of the acquired neural signals, and should include a power source with enough energy storage for the minimum duration of uninterrupted experiments.

Size, power consumption, robustness, input referred noise, and bandwidth are the main concerns in developing wireless neural recording (WNR) systems, and several groups have tried to tackle them in different ways. Nevertheless, WNR systems are still generally absent in electrophysiology labs. The majority of the neuroscientists are willing to adopt WNR systems if they can seamlessly substitute their current hardwired systems at a reasonable cost, setting up effort, maintenance, and additional support.

Currently systems of obtaining neural data and wirelessly transmitting same from the cranial cavity have significant drawbacks. A first conventional system of wirelessly recording and transmitting neural signals is to read the neural signal with an electrode and ultimately transmit the received signal wirelessly in an analog domain. There are many advantages of transmitting in the analog domain, including simplicity of the transmitter unit, preservation of the original waveform amplitudes, low power consumption to transmit information, and the ability to send large amounts of data in smaller packages. Unfortunately, the disadvantages of transmitting in analog outweigh its advantages. When transmitting in analog, the transmitted data is susceptible to noise and interference, which will ultimately reduce the quality of the transmitted signal and in some cases, renders it useless on the receiver side. There are many sources of noise and interference, some of which are internal within the system and some of are imposed from outside. Cross-talk among multiple recording channels, thermal noise, and oscillator phase noise are examples of internal noise. Electromagnetic interference from nearby sources of radio frequency, such as cell phones, and motion artifacts due to movements of the subject, are examples of external noise and interference. After the analog data is transferred, a receiver can convert the analog signal to a digital signal to be analyzed by a digital signal processing (DSP) system, or a computer. On the other hand, to resolve some of the above issues, a second conventional system of wirelessly recording and transmitting neural signals, or any other biological information, brings the analog to digital converter (ADC) block inside the body within the implantable device in order to convert the acquired data from analog format into digital, which is more robust against noise and interference. Digital conversion on the front end also provides the opportunity to compress the data and use the available wireless bandwidth more efficiently. Again, while there are a few advantages, such as more robust and reliable data transmission across the wireless link, the disadvantages outweigh the advantages. By implementing the ADC as part of the implantable device, the power consumption and size of the device increases and adds to the complexity of the implantable device. Digitized data bit stream at high data rates require very accurate timing and synchronization between the transmitter and receiver. If the receiver loses its synchronization with the transmitter, the received data will be lost and cannot be easily recovered. Furthermore, data compression on the transmitter side is not always desired, because it can potentially result in the loss of useful information.

For example, one current system employs commercial off-the-shelf components in their WNR system, particularly to establish the wireless link using the ZigBee and Bluetooth standards. Even though this method can significantly reduce the development time, and has the added benefit of complying with the Federal Communications Commission (FCC) regulations, the size and power overhead in general purpose components may lose their competitive edge in high channel counts.

Other exemplary systems have tried to tackle the bandwidth limitation by processing the neural signals on the transmitter unit by extracting their key features, and only sending a compressed version of the neural data across the wireless link. An important piece of information in a neural signal is the timing of the spike events. Hence, once spikes generated by a specific neuron are detected, one can transmit timing information, as opposed to the entire waveform. The challenge, however, is that the recorded signal from each extra cellular recording site contains spikes from a handful of nearby neurons that are randomly dispersed around the site, as well as those that are far away and their activities contribute to background noise. Spike neural activities should, therefore, be identified from noise and carefully sorted based on their waveforms before they can be converted to "single-unit" activities. To make things even more complicated, there are also gradual changes in the waveforms of the same neurons over time.

The processing power needed for the state-of-the-art spike sorting algorithms that operate on multiple channels in real time has required neuroscientists to employ high performance multi-core computing clusters. Embedding a comparable amount of computational power and programmability on the transmitter unit does not seem to be feasible, at least in the near future. Thus, such architectures are only suitable for neuroprostheses applications, where simple and low power routines would be sufficient. Moreover, many neuroscientists are interested not only in the single-unit activities but also in low frequency components of the neural signals, known as local field potentials (LFP), which are representative of the collective activities of thousands of neurons.

Yet another exemplary system can encode the neural signal amplitude above the noise level in a series of sharp pulses, which frequency is proportional to the signal amplitude. This is a low power encoding scheme and works well for a single or small number of channels. It is not clear, however, how the pulses generated from different channels would be combined to be transmitted across the wireless link.

Still other exemplary systems can combine the sampled neural signals from different channels using time division multiplexing (TDM) and transmitting an analog signal. The advantage of this method is its simplicity and low power consumption. Analog signals, however as mentioned earlier, are susceptible to noise, and the transitions from one channel to another in short sampling periods can result in significant crosstalk among adjacent channels on the receiver side.

To get a sense of how much information needs to be transferred across the wireless link, it is important to note that the neural signal spectrum spans from approximately 0.1 Hz to 10 kHz. Hence, the Nyquist rate requires 20 kilo-Samples per second per channel. Considering that recorded neural signals are often between 50 µV to 1 mV having a supply range of ±1.5 V, and the fact that even in a high quality recording there is often greater than 10 µV of background noise, a resolution of eight to ten bits should be sufficient in this application. Therefore, at least 160 kb/s of bandwidth is needed for raw data per recording channel. In other words, a 100 channel neural recording system, for example, requires a wireless link with 10 Mega-bits per second bandwidth.

SUMMARY

Briefly, described, embodiments of the present invention relate to systems and methods for a wireless neural recording system. Further, embodiments of the present invention relate to a flexible, clockless, plurality-channel simultaneous wireless neural recording system with adjustable resolution. In addition to neural signals, the same system that is described here can be used for other biological signals with electrical nature such as electrocardiogram (ECG), electroencephalogram (EEG), electrocorticogram (ECoG), electromyogram (EMG), electro-oculo-gram (EOG), electrogastrogram (EGG), etc. Further, by adding a transducer in front of the described systems, other non-electrical biological parameters such as blood pressure, body temperature, blood oxygen saturation ($SpO_2$), blood $CO_2$ saturation, NO concentration, respiration, and a variety of positions can be converted to electrical signals and transmitted using embodiments of the present invention.

In an exemplary embodiment, the system tackles bandwidth problems while transferring the complexities from the implantable unit, where size and power are extremely limited, to the external unit. The system also provides a high level of flexibility, allowing a tradeoff among bandwidth, sampling rate, dynamic range, and resolution of the system, depending on the type of the neural signals and the number of active channels.

In an exemplary embodiment, a 32 channel wireless implantable neural recording (WINeR) system-on-a-chip (SoC) uses time division multiplexing (TDM) a pulse width modulated (PWM) sample from every channel, while eliminating the need for large off-chip components, digital buffers, and particularly, the high frequency on-chip clock of conventional systems. This reduces the overall system noise and lowers the complexity and power dissipation on a transmitter of the wireless unit.

One aspect of the present invention is to provide a system for transmitting bioelectrical signals. The system includes an implantable bioelectrical sensor for receiving at least one bioelectrical signal; an analog-to-time converter for converting the received bioelectrical signal from an analog domain to a time domain signal; and a radio frequency (RF) modulator for transmitting the time domain signal. The analog-to-time converter and the RF modulator are implantable in a living being.

These and other objects, features, and advantages of the electronic display system will become more apparent upon reading the following specification in conjunction with the accompanying drawing figures.

BRIEF DESCRIPTION OF THE DRAWINGS

FIGS. 7A-7B illustrate exemplary graphical representations of triangular waveforms generated with the TWG of FIG. 6A, in accordance with an exemplary embodiment of the present invention.

DETAILED DESCRIPTION

Figure 1:
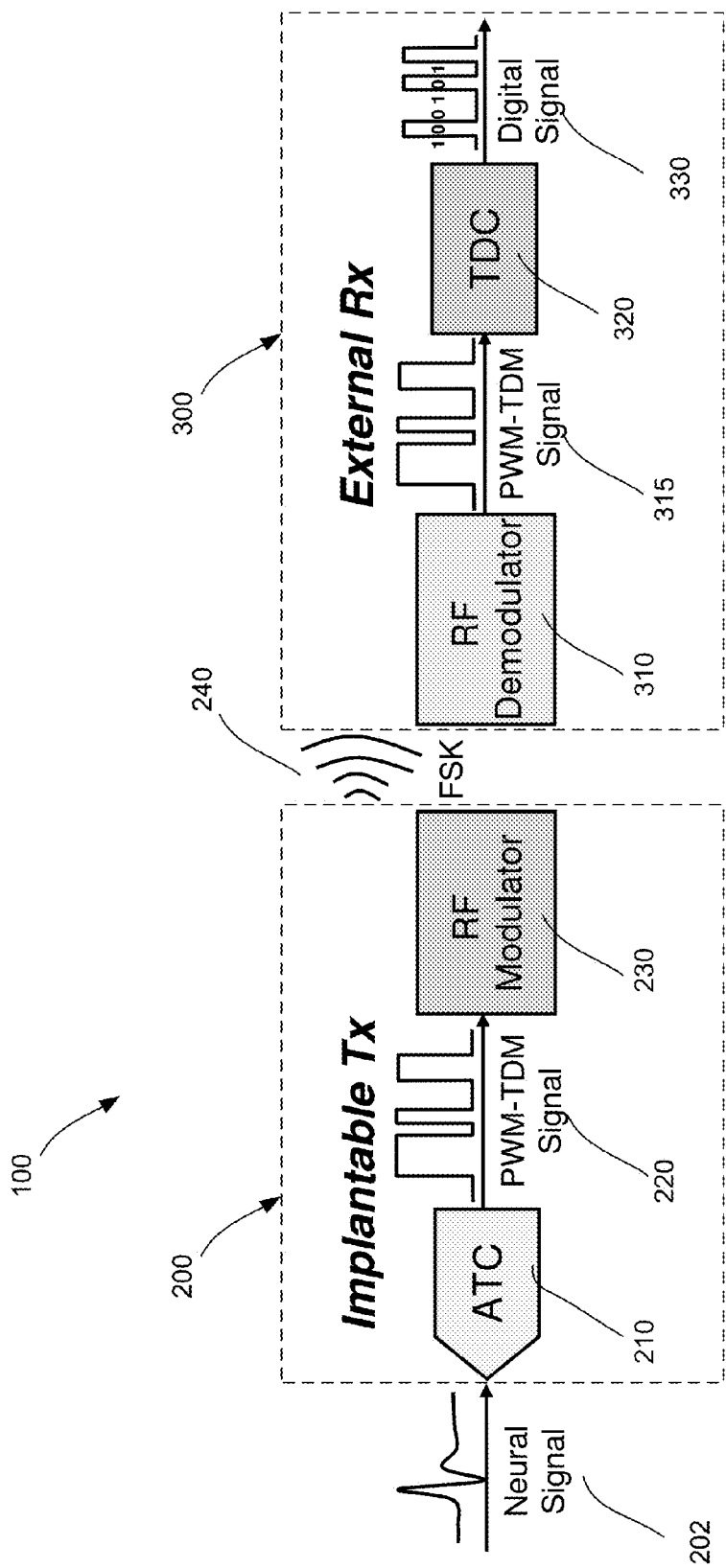
FIG. 1 illustrates a block diagram of a wireless neural recording system, in accordance with an exemplary embodiment of the present invention.

To facilitate an understanding of embodiments, principles, and features of the present invention, they are explained hereinafter with reference to implementation in illustrative embodiments. In particular, they are described in the context of being a wireless implantable neural recording (WINeR) system and method.

Embodiments of the present invention, however, are not limited to use in the described systems. Rather, embodiments of the present invention can be used when a small, low power, and short range wireless recording system is desired or necessary. Thus, the system described hereinafter as a wireless implantable neural recording system method can also find utility as a system for many applications beyond neural signals, including but not limited to other analog bioelectrical signals.

The components described hereinafter as making up the various embodiments are intended to be illustrative and not restrictive. Many suitable components that would perform the same or a similar function as the materials described herein are intended to be embraced within the scope of embodiments of the present invention.

Embodiments of the present invention overcome the deficiencies in the prior art. Embodiments of the present invention overcome the current multi-channel neural recording systems, whether for research on animal subjects or for a clinical application on human, that are hard wired. By eliminating these wires with a wireless system, embodiments of the present invention improve the signal to noise ratio (SNR), reduce the tethering effect on the animal/human subject, and allow behavioral neuroscience researchers to use multiple animals/humans in their experiments/clinical trials. For humans, the benefits include hiding the instrumentalities for better aesthetics, additional comfort of not having transcutaneous wires breaking through the skin, and reducing, if not eliminating, the risk of potential harmful contaminants from entering the body, e.g., the brain.

Accordingly, embodiments of the present invention improve SNR; reduce motion artifacts; eliminate the tethering effect, which can bias animal/human behavior; allow a wider range of experiments with multiple animal/human subjects versus other wired or other wireless systems; reduce the risk of infection on the animal/human; reduce the risk of damage both to the animal/human and to the implanted system; improve a user (animal/human) comfort level; enhance mobility of the animal/human; and makes the system more cosmetically acceptable/pleasing.

A wireless neural recording system is faced with many challenges. First, extracellular neural signals are weak and have one of the widest bandwidth of bioelectrical signals in the body. For example, the neural signals include peak-to-peak amplitude of approximately 50 to 1000 microVolts ($\mu V$), a neural background noise of approximately 5 to 10 microVolts root-mean-squared ($\mu V_{rms}$), frequency contents of 0.1 Hertz (Hz) to 10 kiloHertz (kHz), and a direct current (DC) baseline drifts up to several hundreds of millivolts (mV). Second, any system that is implantable inside the body can cause tissue damage if it increases the local temperature by more than 2 degrees centigrade (° C.), so the power must be less than approximately 80 mW/cm$^2$ (milliWatts per square centimeter). Embodiments of the present invention do not increase the temperature of the living being in which the system is implanted by more than three degrees centigrade. Third, the system should have an extended battery life for chronic experiments, as the user (animal/human) does not want to face numerous surgeries to replace the power source therein. Accordingly, ultra low power consumption is needed for long battery life and to eliminate tissue damage due to high temperatures (heat). Fourth, the system must have a small footprint. Specifically, for systems that are intended for placement in the cranial cavity, the system should be less than one cubic centimeter (1 cm$^3$), depending on the anatomical position. The smaller the implantable system is the better. In particular, the less invasive the system is on the body, the easier the surgery for implanting the system, the less discomfort of the user, and, accordingly, the higher the safety levels of implanting the same.

To handle multiple channels simultaneously and transmit all the required information outside the brain for further processing, a wide bandwidth is needed throughout the system. Specifically, a wide bandwidth is needed from the electrodes through the processing system. For example, for a single channel, having a sampling rate of 20 kSps (kiloSamples per second) and 8 bits of resolution, a data rate of approximately 0.16 Mbps is needed. For 32 channels, however, with a sampling rate of 640 kSps, a data rate of 5.12 Mbps (up to 7 Mbps if the wireless transmission overhead is considered) is needed. Further, unlike air, electromagnetic power absorption in tissue increases as the frequency is squared. Consequently, embodiments of the present invention prefer the carrier frequency to be as low as possible to minimize losses.

With the above challenges in mind, and referring now to the figures, wherein like reference numerals represent like parts throughout the views, embodiments of the present invention will be described in detail. Embodiments of the present invention relate to an implantable transmitter in a brain of a test subject or a user, e.g., an animal or a human, that is as simple, small, and low power as possible for recording neural signals. The simplicity, size and low power consumption of the transmitter is preferably simplified, at the cost of making the external receiver to be more complex. By adding to the complexity of the external receiver, the size and power of the implantable transmitter can be controlled and, thus, reduced. And since the external receiver is located outside the cranial cavity, the size and power are not as critical as the implanted transmitter which is inside the body.

Embodiments of the present invention relate to a wireless implantable neural recording system. As shown in FIG. 1, the system 100 includes a front-end or implantable transmitter 200, and a back-end, or external receiver 300.

The transmitter 200 receives a neural (or biological, or bioelectrical) signal or a plurality of neural (or biological) signals 202 from one or more electrodes 110 implanted in the brain. An electrode 110 can be coupled directly to a neuron or, alternatively, be placed within neural circuitry and thus nearby a number of neurons. An analog to time converter (ATC) 210 can receive the neural signals 202, which are converted to a pulse width modulated time division multiplexer (PWM-TDM) signal 220. A radio frequency (RF) modulator 230 transmits a signal 240, e.g., frequency shift keyed (FSK), therefrom.

The receiver 300, on the other hand, receives the signal 240 and directs it to a RF demodulator 310 to recover the base band PWM-TDM signal 315, which can be a replica of the PWM-TDM signal 220 sent by the transmitter 200. The recovered PWM-TDM signal 315 is converted to a digital signal 330 with a time to digital converter (TDC) 320, which is then processed by a processing system that receives the digital signal 330, such a computer or like device.

The transmitter 200 converts an analog sample to time by pulse width modulation (PWM), and carries the data in the pulse duty cycle, which is the ratio between the duration of the signal when it is high to the total duration of a cycle (high+ low). The PWM-TDM signal 220 can then be frequency modulated (FM) and the resulting FSK signal 240 is transmitted across a wireless link. The receiver 300 converts the pulse duty cycle to digital data 330. In other words, the transmitter 200 coverts the analog neural (or biological) signal 202 to a time events, and the receiver 300 coverts the time events to a digital signal 330. The result is simple to implement, robust, and monotonic.

In an exemplary embodiment, the transmitter 200 does not require an on-chip clock, which is required in conventional wireless solutions and can contaminate analog samples, require additional power consumption, and further increase its footprint. In an exemplary embodiment, the transmitter can include an analog to asynchronous converter, which like the ATC does not need a clock signal. For example, the bioelectrical signals can be received by an analog to asynchronous converter for converting the received bioelectrical signal to an asynchronous signal, which can ultimately be transmitted. By transmitting an asynchronous converted signal can be wirelessly transmitted, and the data transferred, like in the ATC system, is not lost.

Figure 2A:
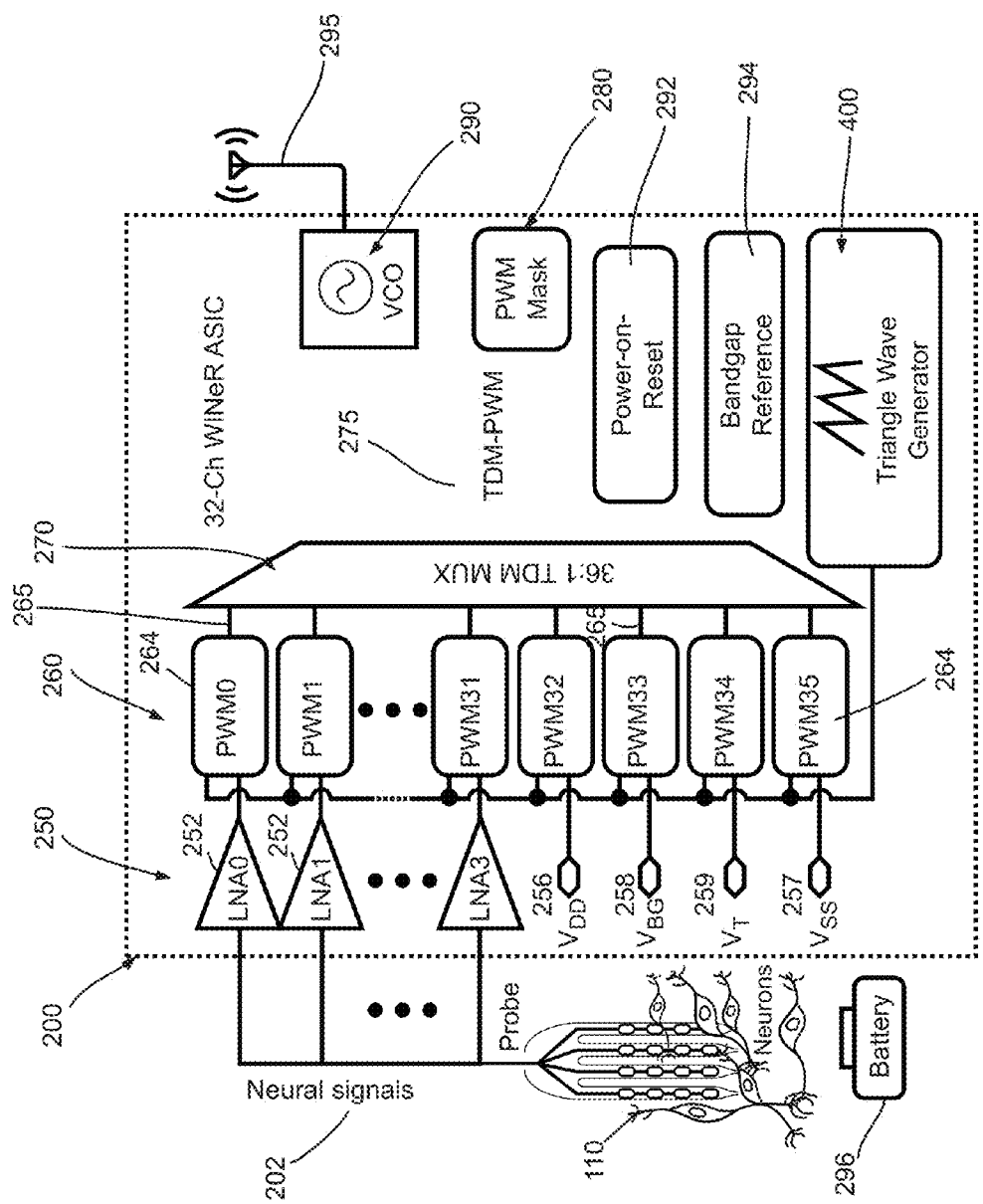
FIG. 2A illustrates a block diagram of a transmitter unit of the wireless neural recording system of FIG. 1, in accordance with an exemplary embodiment of the present invention.

Referring now to FIG. 2A, a block-diagram schematic of the transmitter 200 is illustrated, in accordance with an exemplary embodiment of the present invention. The transmitter 200 includes a front end amplifier block 250 comprising a plurality of low noise amplifiers (LNAs) 252, a pulse width modulator block 260 comprising a plurality of pulse width modulators 264, a multiplexer 270, a pulse width modulation mask 280, a voltage controlled oscillator (VCO) 290, a power-on reset circuit 292, a bandgap reference 294, a power source, such as battery 296, and a triangular waveform generator 400.

In operation, neural signals 202 from one or more microelectrode arrays 110, which are implanted in the brain, are amplified and bandpass filtered by the front-end amplifier 250 comprising the array of tunable LNAs 252. The conditioned neural signals are then pulse width modulated by the pulse width modulators 264, each comprising an array of high speed comparators 262, which can also receive a precision triangular waveform from the triangular waveform generator 400. The pulse width modulated samples are time-division multiplexed by the multiplexer 270 along with samples of the monitoring signals, including $V_{DD}$, $V_{SS}$, the bandgap reference voltage ($V_{BG}$) and the temperature voltage ($V_T$). Then, a plurality of sampled pulses of TDM-PWM signal are masked with a pulse width modulation mask 280, and fed into a voltage controlled oscillator 290.

In an exemplary embodiment, the transmitter 200 can receive a plurality of channels, via a plurality of electrodes 110 (e.g., an electrode array). For example, there can be 32 electrodes positioned in a user's brain receiving neural signals 202, and then prepared for transmission and thus ultimately transmitted by the transmitter 200. In an exemplary embodiment, the transmitter 200 can be implemented as a 32 channel application specific integrated circuit (ASIC).

More specifically, when the neural signals 202 arrive at the transmitter 200 they are loaded into a front-end amplifier block 250. The analog front-end amplifier 250 of the transmitter 200 can include a plurality of two-stage capacitively coupled LNAs 252. Each LNA 252 includes built-in bandpass filtering capability. Accordingly, the LNAs amplify the received neural signals, preferably in the frequency range of approximately 0.1 Hz to approximately 10 kHz. In an exemplary embodiment, there can be a plurality of channels of neural signals fed from the electrodes into an equal plurality LNAs for amplifying and filtering the neural signals. For example, there can be 32 channels of neural signals fed from the electrodes into 32 LNAs for amplifying and filtering each neural signal.

Figure 3:
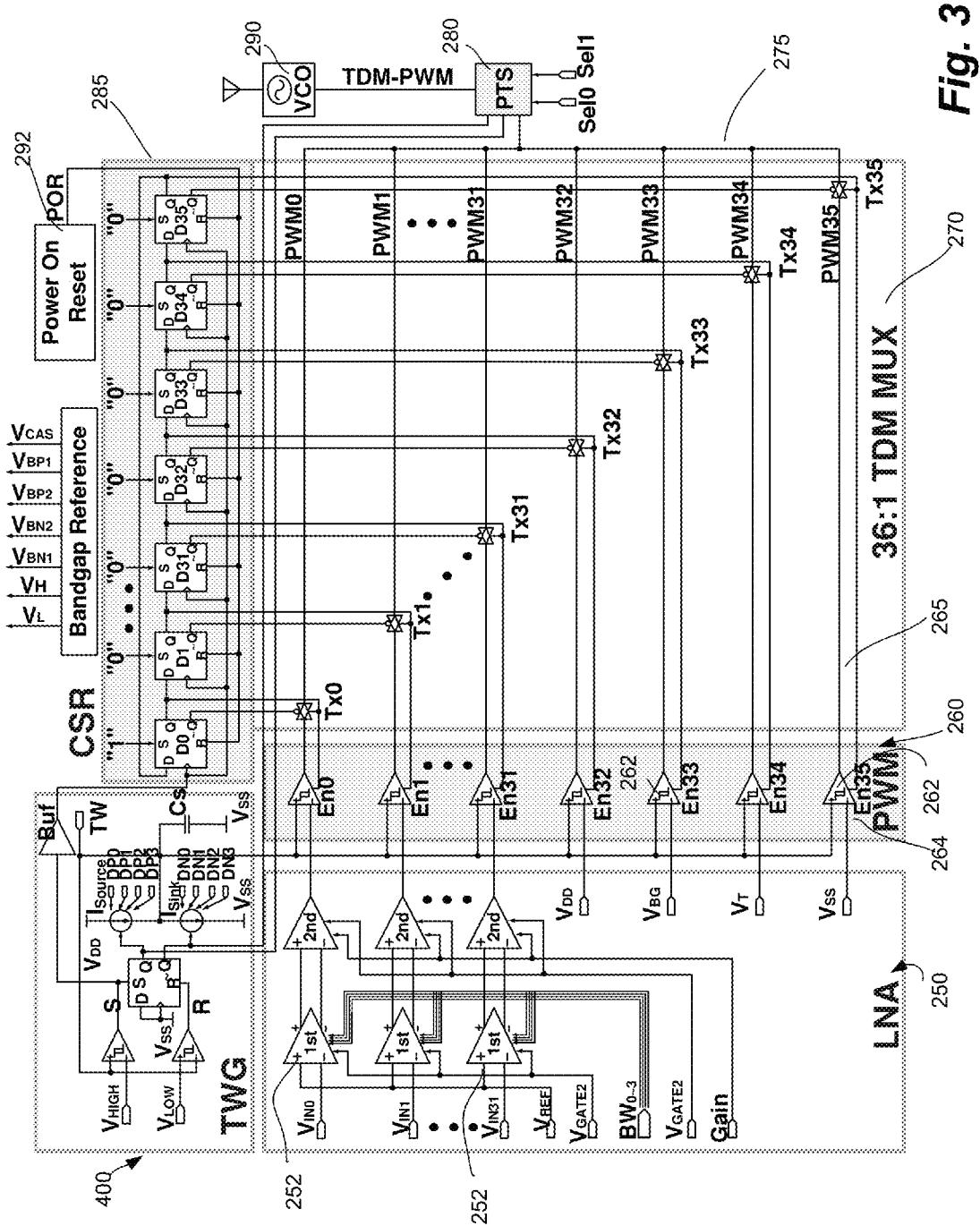
FIG. 3 illustrates a more detailed partial schematic of the transmitter of FIG. 2A, in accordance with an exemplary embodiment of the present invention.

After the neural signals 202 are amplified and filtered by the front-end amplifier block 250, the signals are fed into a plurality of pulse width modulators 260. The amplifier outputs are combined with the four monitoring signals, e.g., $V_{DD}$ 256, $V_{SS}$ 257, the bandgap reference voltage ($V_{BG}$) 258 and the temperature voltage ($V_T$) 259, and fed into the pulse width modulator block 260. In an exemplary embodiment of a 32 channel system, there are 36 pulse width modulators (PWM0-PWM35). As described more fully below, and as illustrated in FIG. 3, each pulse width modulator 264 of the plurality of pulse width modulators 260 includes a rail-to-rail comparator 262. The 32 signals, which have been amplified and filtered by the front-end amplifier block 250, are fed to a pulse width modulator 260, and the four monitoring signals 256, 257, 258, 259 are also each fed to the same pulse width modulator 260. The result are pulse width modulated samples 265.

Each of the pulse width modulated samples 265 are next fed to a time division multiplexer (TDM MUX) 270. The samples 265 are time-division multiplexed along with the samples of the four monitoring signals 256, 257, 258, and 259 (i.e. placed back-to-back in series) to form a PWM-TDM signal 275. In an exemplary embodiment comprising 32 channels, the 32 pulse width modulated samples and the samples of the four monitoring signals are selected one at a time to create the TDM-PWM signal 275 by a circular shift register (CSR) running a 36:1 MUX. The CSR receives a time base from the triangular waveform generator 400 as its clock signal.

Figure 4:
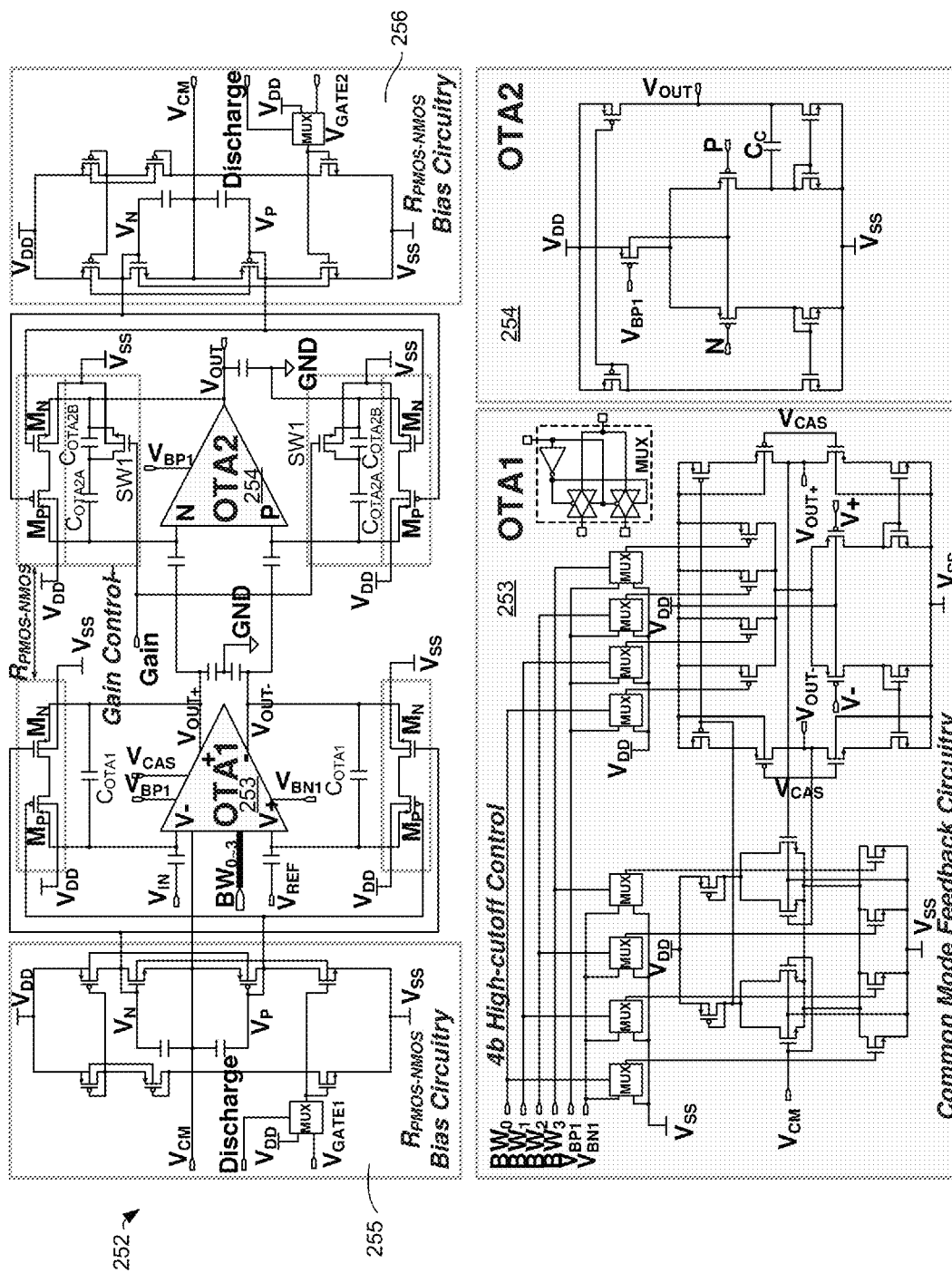
FIG. 4 illustrates a schematic of a low noise amplifier (LNA) of the transmitter of FIG. 2A, in accordance with an exemplary embodiment of the present invention.

FIG. 4 shows a detailed schematic diagram of one of the LNAs which can both amplify and filter the neural or biological signals.

Because the transmitter 200 does not include a clock, which is one of the advantages of embodiments of the present invention, the triangular waveform generator (TWG) 400 is provided. For example, the TWG 400, which is shown in more detail in FIG. 5, directly affects the noise, accuracy, and resolution of the system. In an exemplary embodiment, and as illustrated in FIGS. 6A-6C, a precision TWG 400 includes a binary weighted, high voltage compliance, large output impedance complementary current source/sink (CCSS) pair, which linearly charges/discharges a capacitor ($C_S$) having a capacitance of approximately 10 pico Farad (pF).

In an exemplary embodiment, the CCSS circuit of the TWG 400 utilizes MOSFETs in deep triode region. By controlling the binary inputs $DP_{0-3}$ and $DN_{0-3}$, $I_{Source}$ and $I_{Sink}$ can each be varied in approximately 16 steps. Controlling both charging and discharging of the capacitor not only avoids substrate charge injection, but also provides programmability over the sampling rate in a wide range. A window detector limits the TWG output and generates the switching signals for the CCSS, CSR, and TDM blocks. The lower and upper voltage limits, $V_{low}$ and $V_{high}$, can be either generated internally ($V_{SS}+0.1$ V and $V_{DD}-0.1$ V) or adjusted externally based on the dynamic range of the amplified neural signals.

Referring back to FIG. 2A, after the samples 265 are multiplexed by the TDM-PWM MUX 270, the resulting PWM-TDM signal 275 is fed to a PWM mask 280. The PWM mask 280 can be responsible for limiting the PWM-TDM signal to either rising or falling ramps of the triangular wave by masking the opposing side. This synchronizes the PWM pulses at their rising or falling edges, improving the system accuracy and facilitating data recovery on the receiver 300. Another function of the mask 280 is enforcing the minimum and maximum widths of the PWM pulses, to reduce the required wireless link bandwidth and improve the system resolution by avoiding pulse widths that are too narrow.

After the samples are masked, they are fed to the voltage controlled oscillator (VCO) 290. In an exemplary embodiment, trimmed PWM-TDM samples drive the VCO 290, which may include an off-chip surface mount device (SMD)

inductor. In an exemplary embodiment, the VCO 290 can operate in two modes: 1) wideband frequency shift keying (FSK) when the varactor input is driven, or 2) wideband on-off keying (OOK) when the VCO enable input is driven.

Figure 2B:
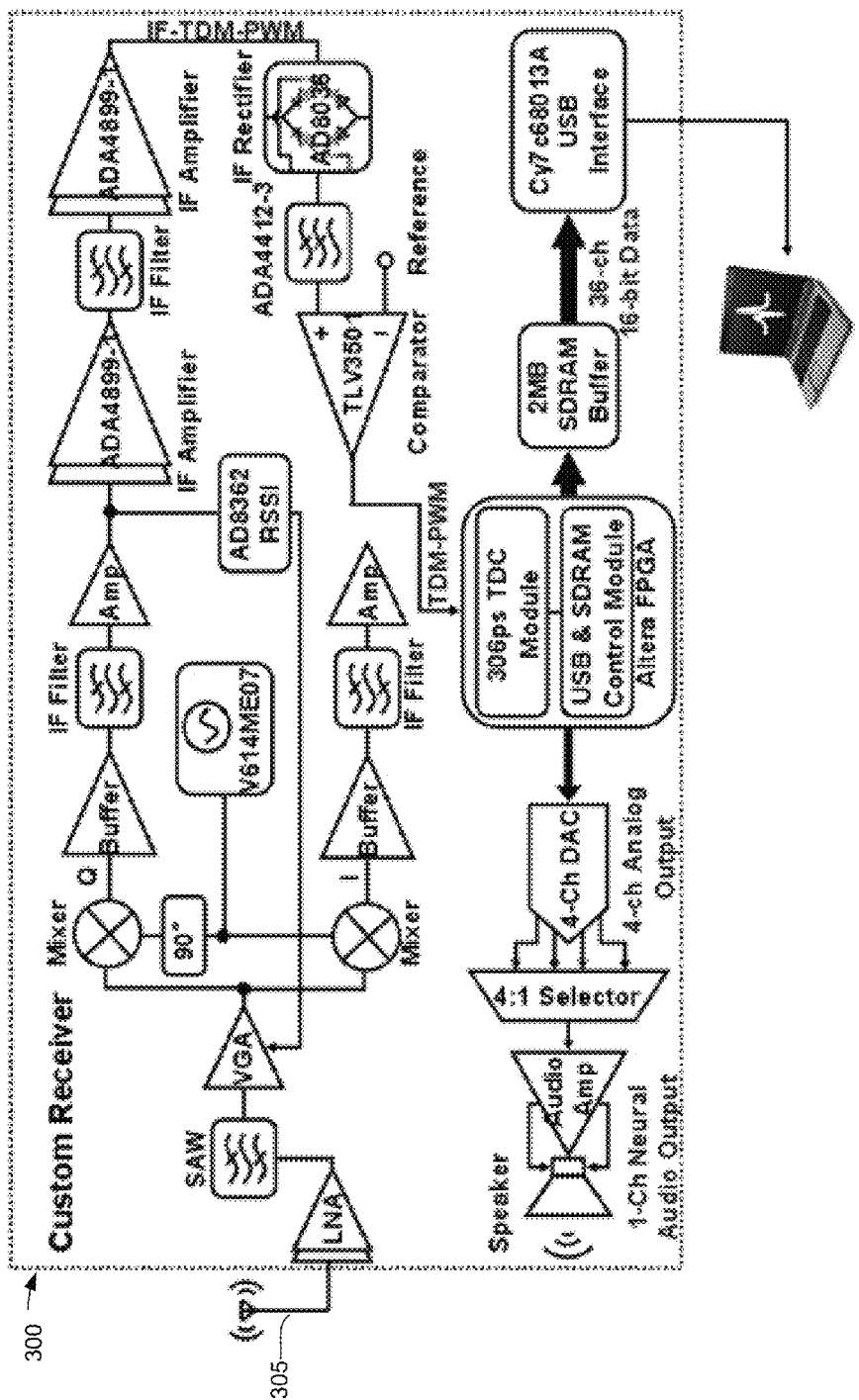
FIG. 2B illustrates a block diagram of a receiver unit of the wireless neural recording system of FIG. 1, in accordance with an exemplary embodiment of the present invention.

The samples from the VCO 290 are then transmitted from an antenna 295. As shown in FIG. 2B, the receiver 300 can receive the transmitted sample with its own antenna 305. The receiver 300 down converts the RF-FSK and FM demodulates it through, for example, a discriminator. The recovered TDM-PWM 315 is then fed to a TDC for converting the time signal to a digital signal. In an exemplary embodiment, the TDC can be implemented on a FPGA board for digitization. Digital values can be buffered in a memory, e.g., 2 MB SRAM, ensuring continuity and then forwarded to processing system, such as a computer, via an interface, such as a USB (universal serial bus) interface or like system. Ultimately, each sample frame received by the computer can be detected using the unique pattern of the monitoring samples, and a graphical user interface (GUI) can illustrate the individual channels after time division demultiplexing. The receiver 300 may be equipped with an X number of channel—(e.g., four) digital to analog converter (DAC), which can directly generate X analog neural signal outputs to be observed on an oscilloscope. In addition, at least one of these channels may be further amplified to drive a loudspeaker.

In more detail, the receiver 300 can include the antenna 305 for receiving the samples; the receiver 300 is adapted to convert the time sample to a digital signal. Initially, the receiver 300 receives the transmitted signal 240. Then, the received signal, e.g., the FSK-TDM-PWM carrier, can be amplified and filtered by a wideband receiver RF front-end. A mixer can down convert the received carrier to an intermediate frequency (IF) band, which is power stabilized by an automatic gain control (AGC) block within approximately ±0.5 dB. The IF-TDM-PWM may be rectified and low pass filtered with selectable bandwidths, for example, of one of approximately 9, 18, or 36 MHz, to recover the baseband TDM-PWM 315. The edges of this signal may then be sharpened by a high speed comparator (e.g., TVL3501). An FPGA-based time-to-digital converter (TDC) with approximately 0.3 ns resolution may convert the TDM-PWM into a series of 16-bit digitized samples, buffer them through memory, and feed them to a PC via USB for storage, further processing and visualization. The receiver may further include a digital to analog converter (DAC) block, enabling selection of, for example, four out of 32 channels, and convert them to analog signals. These four channels can be monitored in real time, e.g., via an oscilloscope, independent of the processing system. One of these signals may be audio amplified to drive a speaker for the user to hear the "sound" of neurons.

Referring now to FIG. 3, a schematic of the transmitter 200 is illustrated, in accordance with an exemplary embodiment of the present invention. As illustrated in FIG. 2A and described above, the neural signal 202 is received by the transmitter 200 and both amplified and filtered by the front-end amplifier block 250. The amplified signal is then fed to the pulse width modulator block 260, which can also receive the triangular waveform from the TWG 400. Then, the PWM samples 265 are fed to the TDM-PWM MUX 270, and then to the PWM mask 280, and ultimately to the VCO 290 before being transmitted.

As shown in FIGS. 3 and 4, the plurality of LNAs 252 can include two stages. A first stage of the LNA can be fully differential with a fixed approximately 40 dB gain and common-mode feedback (CMFB). The first stage can dissipate approximately 16.4 µA from an approximate ±1.5 V supply. A second stage of the LNA is a differential to single-ended amplifier with a one-bit adjustable gain, e.g., approximately 28 or 37 dB, and can draw approximately 8.1 µA. The low-cutoff of the LNA stage is continuously tunable by changing gate voltages (e.g., $V_{gate1,2}$) of the bidirectional current sources, driving a pair of pseudo-resistors across the capacitive feedback. The high-cutoff is four-bit programmable.

Referring to FIG. 3, as for the PWM block 260, each pulse width modulator 264 comprises a comparator 262. The comparators 262 within the PWM block 260 are enabled one at a time by circulating a "1" in the CSR 285, converting the conditioned analog signals into pulses by comparing them with the output of a precision TWG 400. During each comparison, the substrate is quiet and there is no digital transition, reducing the substrate noise and dynamic power dissipation. In addition to feedback, the monitoring signals provide a unique pattern that can be used to indicate the beginning of each TDM packet on the receiver 300.

The TDM-PWM MUX 270 receives the pulse width sample 265. In an exemplary embodiment, at the global reset, the CSR 285 is loaded with 36-bit binary 10 . . . 00. When the system is running, the single "1" circulates in the CSR 285 and connects one out of the 36 comparator PWM pulses 265 to the MUX 270 output. The resulting signal is a TDM-PWM signal 275, which is buffered and fed into the VCO 290 after being trimmed and synchronized. This architecture significantly facilitates the extension of the system, e.g., to 64 or 128 or more channels, without requiring much additional circuitry.

The PWM mask 280 is responsible for limiting the PWM-TDM signal to either rising or falling ramps of the triangular wave by masking the other side. It synchronizes the PWM pulses at their rising or falling edge, improving the accuracy and facilitating data recovery on the receiver 300. The PWM mask 280 further enforces minimum and maximum widths of the PWM pulses 220, to reduce the required wireless link bandwidth and improve the system resolution by avoiding too narrow pulse widths.

Then, the VCO 290 receives the trimmed PWM-TDM signal to output a signal, such as a FSK signal or an OOK signal. The antenna 295 is adapted to transmit such a signal.

As for the front-end amplifier block 250, each LNA 252 has a novel gain control. As illustrated in FIG. 4, the LNA 252 comprises two OTAs: a first OTA (OTA1) 253 and a second OTA (OTA2) 254. The gain of the first OTA 253 is constant, and can be approximately 40 dB (i.e., 100). The gain of the second OTA 254, however, is programmable, and can be approximately 28 or 37 dB (i.e., 25 or 70). Accordingly, for example, each LNA 252 includes a two-stage LNA block with a total gain of approximately 68 or 77 dB (i.e. 2500 or 7000). Both stages have a capacitive feedback and are AC coupled. Further, the LNA 252 has a low cutoff frequency, which is continuously tunable from approximately 0.1 Hz to approximately 1 kHz through $V_{gate1}$ and $V_{gate2}$, and a high cutoff frequency that can be digitally tuned from 0.7 to 10 kHz through $BW_0$ to $BW_3$. The LNA 252 input referred noise can be approximately 3.9 $\mu V_{rms}$ in an approximately 10 Hz to approximately 10 kHz frequency range.

As also illustrated in FIG. 4, the LNA 252 includes a first bias circuit 255, a second bias circuit 256, OTA1 253, OTA2 254, and connection circuitry. Both bias circuits provide bidirectional current sources. The feedback of the OTA1 253 and OTA2 254 create very high impedance. To maintain the gain of OTA1 253 constant, a PMOS transistor $M_P$ and a NMOS transistor $M_N$ are in series and their combination is in parallel with a fixed capacitor $C_{OTA1}$. Such feedbacks can be implemented across both the positive and negative ends of the fully differential OTA 253. On the other hand, OTA2 254 has a programmable feedback that can be changed. The feedback across OTA2 254 also includes the PMOS transistor $M_P$ and the NMOS transistor $M_N$ in series. These transistors, however, are in parallel with a first capacitor $C_{OTA2A}$, which is in series with a second capacitor $C_{OTA2B}$ that is in parallel with a switch SW1. The feedback across OTA2 254 is essentially a resistor-capacitive delay. The transistors ($M_P$ and $M_N$) provide the resistance, and the first and second capacitors ($C_{OTA2A}$ and $C_{OTA2B}$) provide the capacitance. When the switch SW1 is off (i.e. open), the second capacitor $C_{OTA2B}$, which is parallel with switch SW1, can charge and thus the total capacitance in parallel with $M_P$ and $M_N$ is smaller. On the other hand, when the switch SW1 is on (i.e. closed), the second capacitor $C_{OTA2B}$ does not charge, and thus is shorted for a larger capacitance in parallel with $M_P$ and $M_N$. Ultimately, the switch is controlled by the Gain signal.

Figure 5:
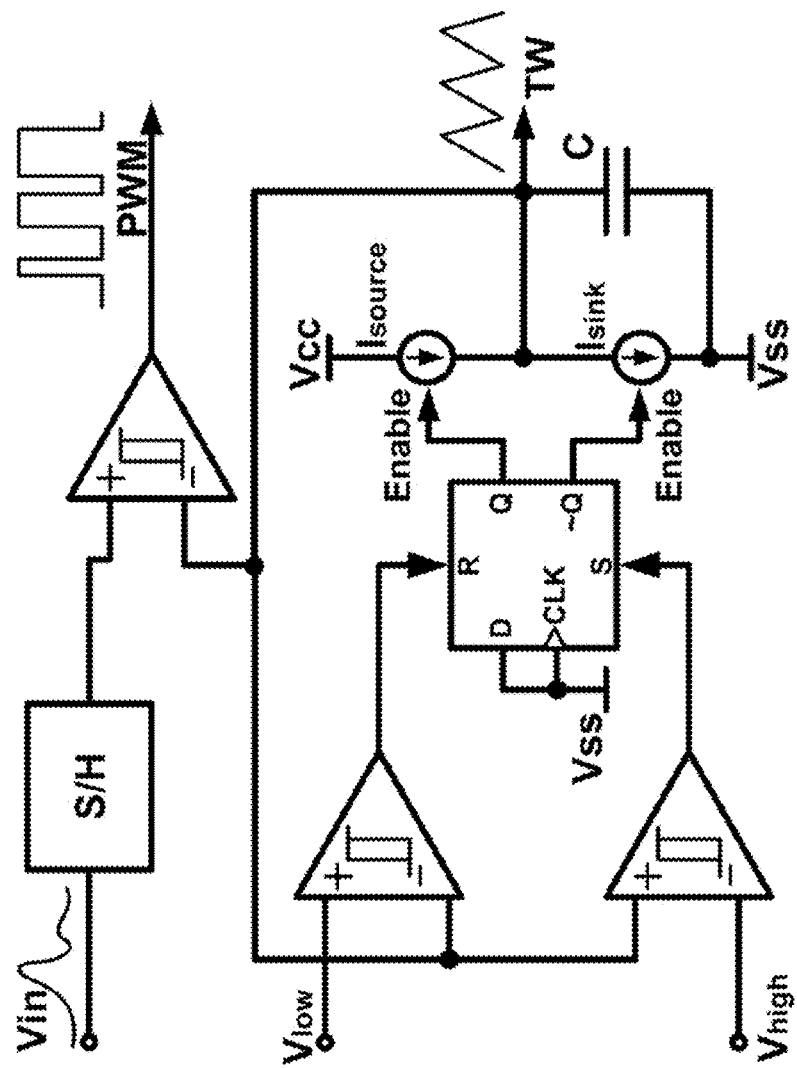
FIG. 5 illustrates a schematic of pulse width modulator (PWM), in accordance with an exemplary embodiment of the present invention.
Figures 6A, 6B, 6C:
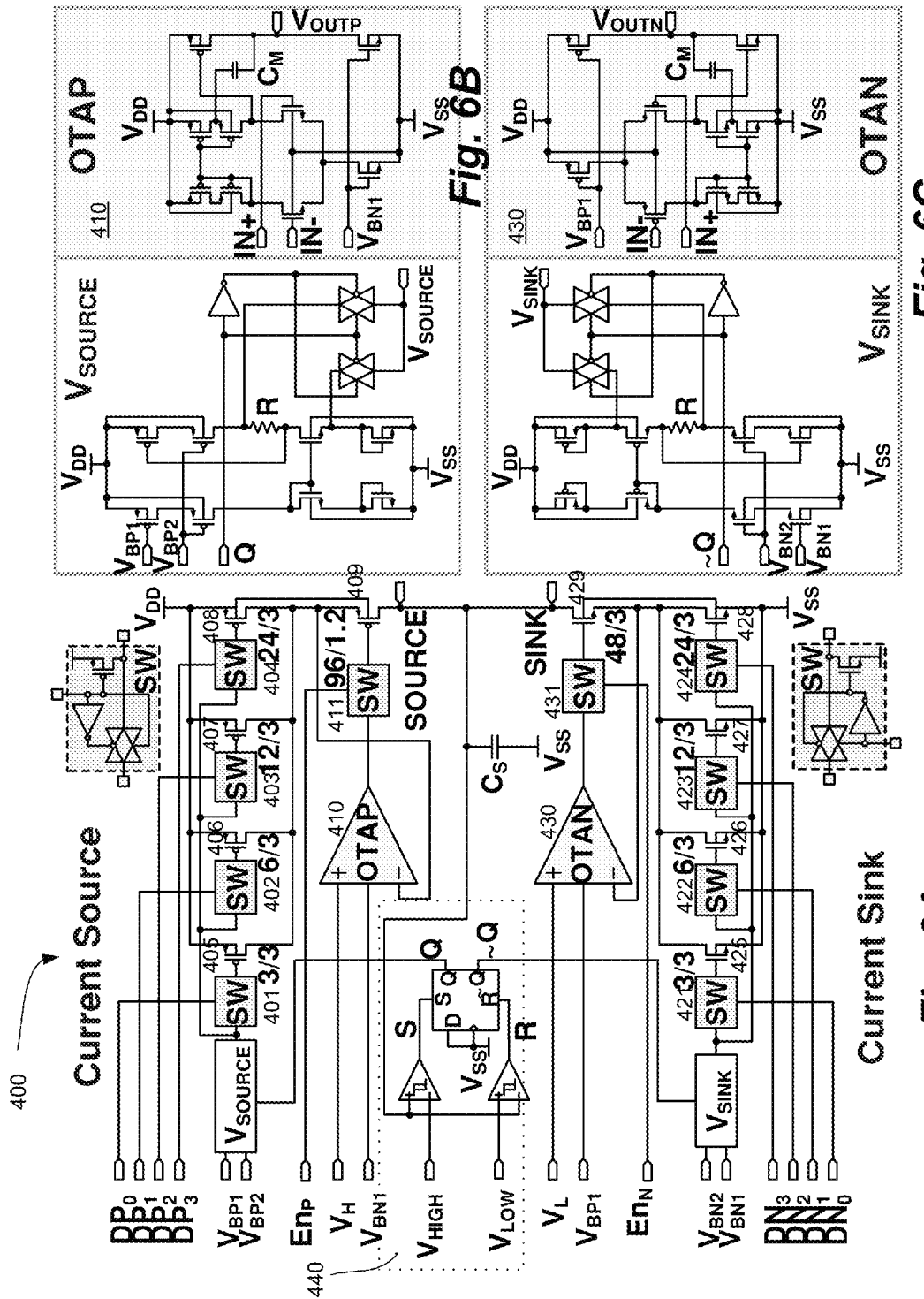
FIG. 6A illustrates a schematic of a triangular waveform generator (TWG), in accordance with an exemplary embodiment of the present invention.
FIG. 6B illustrates a schematic of a P-type current source operational transconductance amplifier (OTAP) for the triangular waveform generator, in accordance with an exemplary embodiment of the present invention.
FIG. 6C illustrates a schematic of an N-type current sink operational transconductance amplifier (OTAN) for the triangular waveform generator, in accordance with an exemplary embodiment of the present invention.

FIG. 5 illustrates a simplified schematic of a TWG 400 and PWM that may be implemented with the present system. The PWM 260 receives the amplified and filtered neural signals, as well as the signal from the TWG 400.

FIG. 6 illustrates a schematic of an exemplary triangular waveform generator (TWG), in accordance with an exemplary embodiment of the present invention. A variety of generators may be used to generate a triangular waveform; the present example is to show but one suitable design.

The TWG 400 includes a pair of programmable complementary current source and sink (CCSS), which have large compliance voltages that may be close to the supply levels. In an exemplary embodiment, the output impedance of the current source and the current sink are quite high, e.g., approximately 17.6 MΩ and 26.6 MΩ, respectively. The CCSS linearly charge and discharge a capacitor ($C_S$), e.g., approximately 6 pF, at an adjustable rate from approximately 58 kHz to approximately 680 kHz.

On the current source end of the CCSS of the TWG, four PMOS devices are inputs to four switches. DP0 is an input for a first switch 401 controlling the status ("on" and "off") of a PMOS transistor 405, which has an exemplary size of 3 μm/3 μm; DP1 is an input for a second switch 402 controlling the status of a PMOS transistor 406, which has an exemplary size of 6 μm/3 μm; DP2 is an input for a third switch 403 controlling the status of a PMOS transistor 407 having an exemplary size of 12 μm/3 μm; and DP3 is an input for a fourth switch 404 controlling the status of a PMOS transistor 408 which has an exemplary size of 24 μm/3 μm. Two voltage signals ($V_{BP1}$ and $V_{BP2}$) are inputs from a reference voltage generator, which are inputs to another bias generator ($V_{SOURCE}$) 415 that prepares inputs for the first, second, third, and fourth switches 401, 402, 403, 404. A first PMOS transistor 405 comprises a gate, source and drain. The gate of the first PMOS transistor 405 is coupled to the first switch 401. The source of the first PMOS transistor 405 is coupled to $V_{DD}$. A second PMOS transistor 406 comprises a gate, a source, and a drain. The gate of the second PMOS transistor 406 is coupled to the second switch 402, and its source is coupled to $V_{DD}$. A third PMOS transistor 407 comprises a gate, a source, and a drain. The gate of the third PMOS transistor 407 is coupled to the third switch 403, and its source is coupled to $V_{DD}$. A fourth PMOS transistor 408 comprises a gate, a source, and a drain. The gate of the fourth PMOS transistor 408 is coupled to the fourth switch 404, and its source is coupled to $V_{DD}$. The drain of the first, second, third, and fourth PMOS transistors 405, 406, 407, and 408 are coupled to a source of a fifth transistor 409 and a negative input to a OTAP 410. The OTAP 410 also receives $V_H$ and a $V_{BN1}$ voltage signals. A fifth switch 411 receives the output of OTAP 410 and $En_p$ signal. The fifth switch 411 is also coupled to the gate of the fifth transistor 409. The drain of the fifth transistor 409 generates a SOURCE current signal, which charges a capacitor $C_S$. The capacitor $C_S$ is coupled between the SOURCE signal and $V_{SS}$.

On the current sink end of the CCSS of the TWG, four NMOS devices are inputs to four switches. DN0 is an input for a sixth switch 421 controlling the status ("on" and "off") of a NMOS transistor 425, which has an exemplary size of 3 μm/3 μm; DN1 is an input for a seventh switch 422, controlling the status of a NMOS transistor 426, which has an exemplary size of 6 μm/3 μm; DN2 is an input for an eighth switch 423, controlling the status of a NMOS transistor 427, which has an exemplary size of 12 μm/3 μm; and DN3 is an input for a ninth switch 424 controlling the status of a NMOS transistor 428, which has an exemplary size of 24 μm/3 μm. Two voltage signals ($V_{BN1}$ and $V_{BN2}$) are inputs from a reference voltage generator, which are inputs to another bias generator ($V_{SINK}$) 435 that prepares inputs for the sixth, seventh, eighth, and ninth switches 421, 422, 423, 424. A first NMOS transistor 425 comprises a gate, source and drain. The gate of the first NMOS transistor 425 is coupled to the sixth switch 421. The drain of the first NMOS transistor 425 is coupled to $V_{SS}$. A second NMOS transistor 426 comprises a gate, a source, and a drain. The gate of the second NMOS transistor 426 is coupled to the seventh switch 422, and its drain is coupled to $V_{SS}$. A third NMOS transistor 427 comprises a gate, a source, and a drain. The gate of the third NMOS transistor 427 is coupled to the eighth switch 423, and its drain is coupled to $V_{SS}$. A fourth NMOS transistor 428 comprises a gate, a source, and a drain. The gate of the fourth NMOS transistor 428 is coupled to the ninth switch 424, and its drain is coupled to $V_{SS}$. The source of the first, second, third, and fourth NMOS transistors 425, 426, 427, and 428 are coupled to a source of a fifth NMOS transistor 429 and a negative input to a OTAN 430. The OTAN 430 also receives $V_L$ and a $V_{BP1}$ voltage signals. A tenth switch 431 receives the output of OTAN 430 and the $En_N$ signal. The tenth switch 431 is also coupled to the gate of the fifth NMOS transistor 429. The source of the fifth NMOS transistor 429 generates a SINK current signal, which discharges the capacitor $C_S$. The capacitor $C_S$ is coupled between the SINK signal and $V_{SS}$. In fact the SOURCE and the SINK signal are connected together and both connected to the capacitor $C_S$. In addition, a D-flip flop circuit 440 can help drive the charging and discharging of the capacitor $C_S$. FIGS. 6B-6C are exemplary schematics of features of the OTAP 410 and OTAN 430.

FIGS. 7A-7B illustrate exemplary graphical representations of triangular waveforms generated with the triangular waveform generator 400 of FIG. 6A, in accordance with an exemplary embodiment of the present invention. The system resolution and dynamic range of the system can be adjusted by changing the frequency and amplitude of the triangular waveform, based on the characteristics of the neural signal and user preferences. For example, if the amplified and filtered neural signal (by LNA) is between $V_1$ and $V_2$ of FIGS. 7A-7B, the $V_{high}$ and $V_{low}$ of the triangular waveform can be adjusted to be slightly above and below these levels. This can increase the time-to-digital converter resolution by a certain number of bits. In an exemplary embodiment, if the input signal range is between $V_1$ and $V_2$, then changing the $V_{high}$, $V_{low}$, $I_{source}$, and $I_{sink}$ in the CCSS of the TWG 400 can adjust the triangular waveform to increase the PWM dynamic range. Consequently, the system resolution can improve by $\log_2[(V_{DD}-V_{SS})/(v_1-v_2)]$ bits. In addition, the sampling rate can be similarly adjusted by changing the triangular wave frequency by varying $V_{high}$, $V_{low}$, $I_{source}$, and $I_{sink}$ to desired levels.

Figure 8:
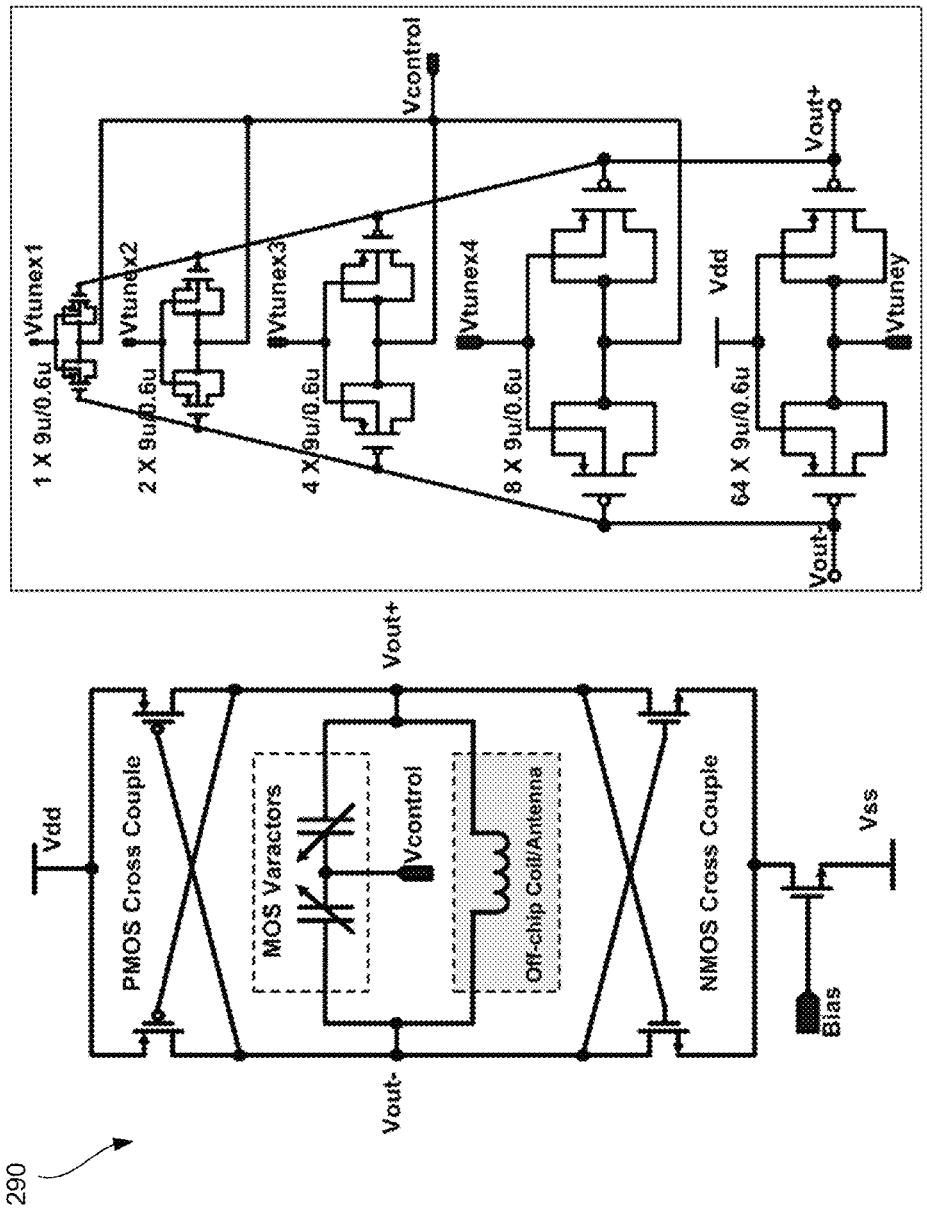
FIG. 8 illustrates a schematic of a voltage controlled oscillator (VCO) of the transmitter of FIG. 2A, in accordance with an exemplary embodiment of the present invention.

FIG. 8 illustrates an exemplary VCO 290 for use in accordance with exemplary embodiments of the present invention. The VCO 290 can be a hybrid VCO with a bank of binary-scaled on-chip varactors (e.g., PMOS), and an off-chip coil. By implementing the VCO with such a design, the result is the flexibility of tuning the VCO carrier frequency, VCO gain, and VCO high gain region. In an exemplary embodiment, the FSK carrier can be tuned at approximately 898 MHz or 926 MHz.

Figure 9:
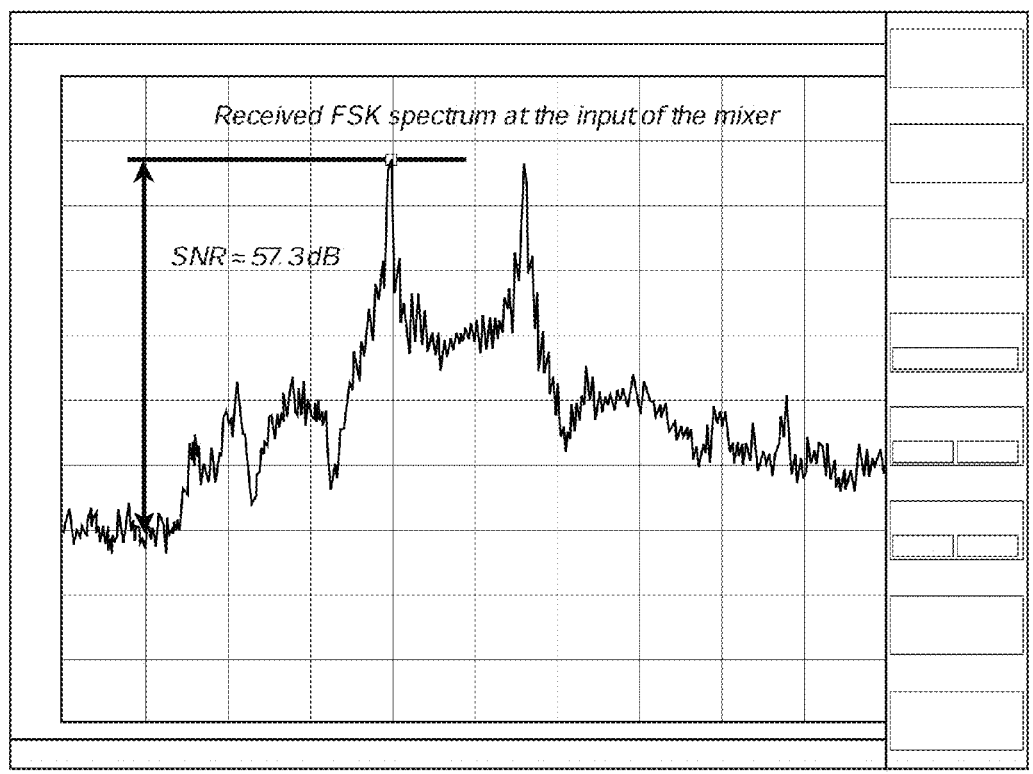
FIG. 9 illustrates a graphical representation of a frequency shift keying (FSK) spectrum, in accordance with an exemplary embodiment of the present invention.

FIG. 9 is a graphical representation of the received FSK spectrum around 900 MHz at the input of the mixer block. As graphically represented in the figure, the SNR is approximately 57.3 dB.

Figure 10:
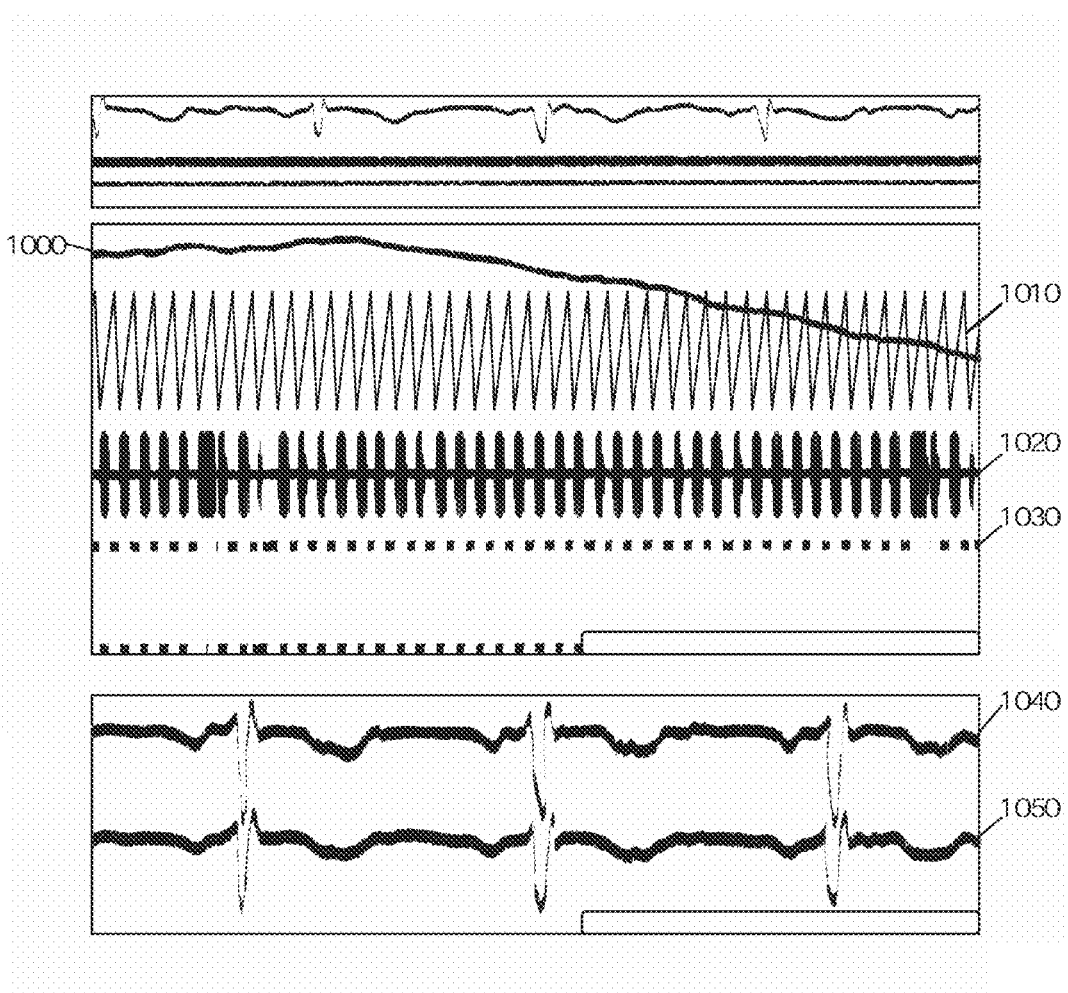
FIG. 10 illustrates graphical representations of various measured waveforms, including a low noise amplifier output, a TWG output, an intermediate frequency (IF) stage-time division multiplexed-pulse width modulated (TDM-PWM) output, a demodulated time division multiplexed-pulse width modulated output, a transmitted low noise amplifier output, and a received digital to analog output, in accordance with an exemplary embodiment of the present invention.

FIG. 10 illustrates graphical representations of various measured waveforms, including (from the top bottom), a low noise amplifier output on the transmitter side, a triangular waveform generator output on the transmitter side, an intermediate frequency-time division multiplexed-pulse width modulated (IF-PWM-TDM) output on the receiver side, a demodulated time division multiplexed-pulse width modulated output on the receiver side, a low noise amplifier output on the transmitter side, and a received and reconstructed version of the same signal at the digital to analog converter (DAC) output, in accordance with an exemplary embodiment of the present invention. These graphical representations are some of the measured waveforms at nodes on the transmitter and receiver sides when an approximately 1.3 mV, 30 Hz artificial ECG signal is applied to the input of the system 100. From the top down, graphical representation 1000 is the LNA output on the transmitter side, graphical representation 1010 is the TWG output on the transmitter side, graphical representation 1020 is the IF-TDM-PWM signal on the receiver side, graphical representation 1030 is the demodulated TDM-PWM signal on the receiver side, graphical representation 1040 is the transmitter LNA output, and graphical representation 1050 is the receiver digital to analog converter output.

Figure 11:
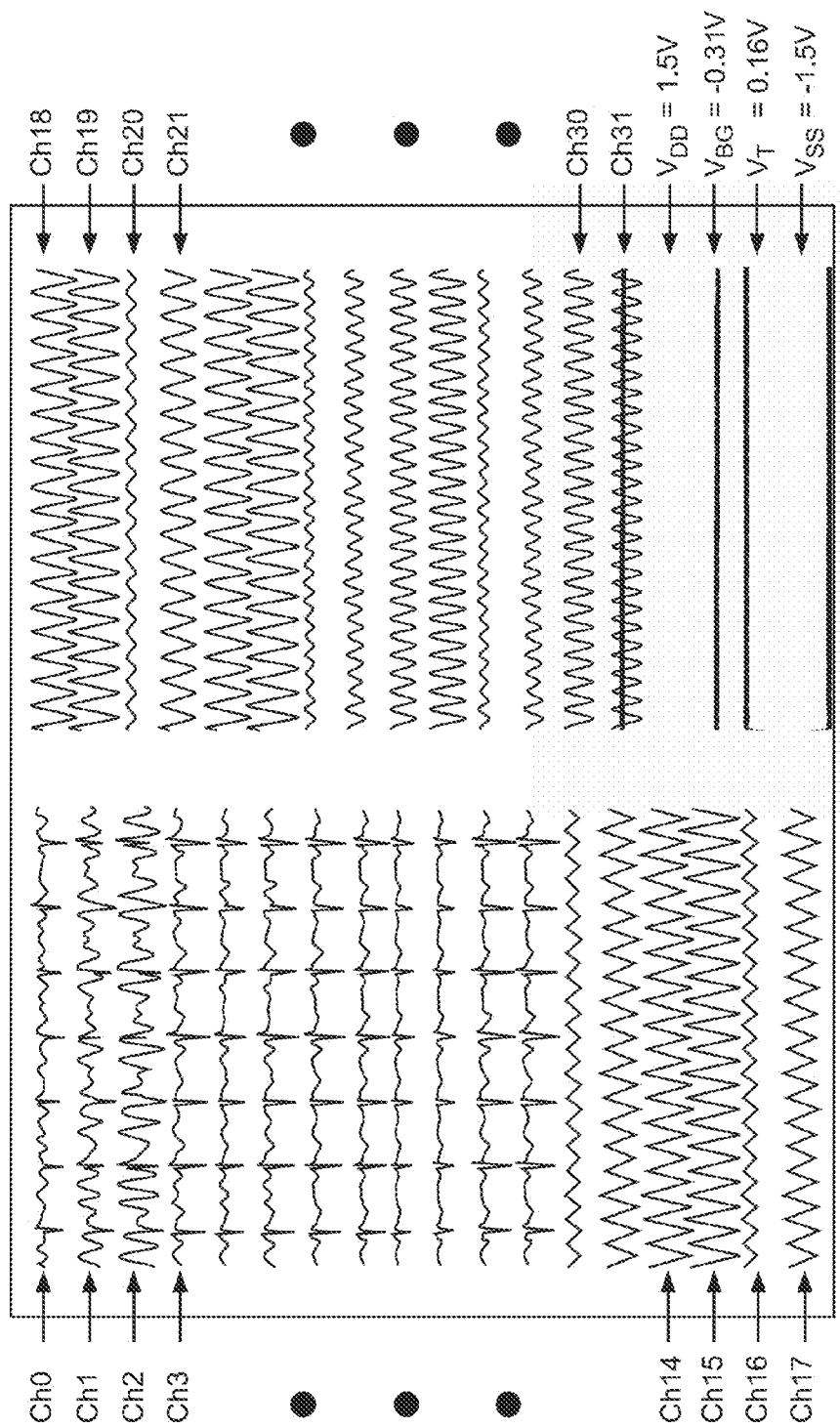
FIG. 11 illustrates a graphical user interface (GUI) representation of 32 arbitrary and four monitoring signals being simultaneously recorded, in accordance with an exemplary embodiment of the present invention.

FIG. 11 illustrates a graphical representation of 32 arbitrary and four monitoring signals being simultaneously recorded, in accordance with an exemplary embodiment of the present invention. This graphical representation depicts a recording sample when three arbitrary waveforms from three function generators are divided below approximately 1 mV and applied to two or three input channels, each. For this measurement, the distance between the transmitter and the receiver antennas was approximately one meter.

Figure 12:
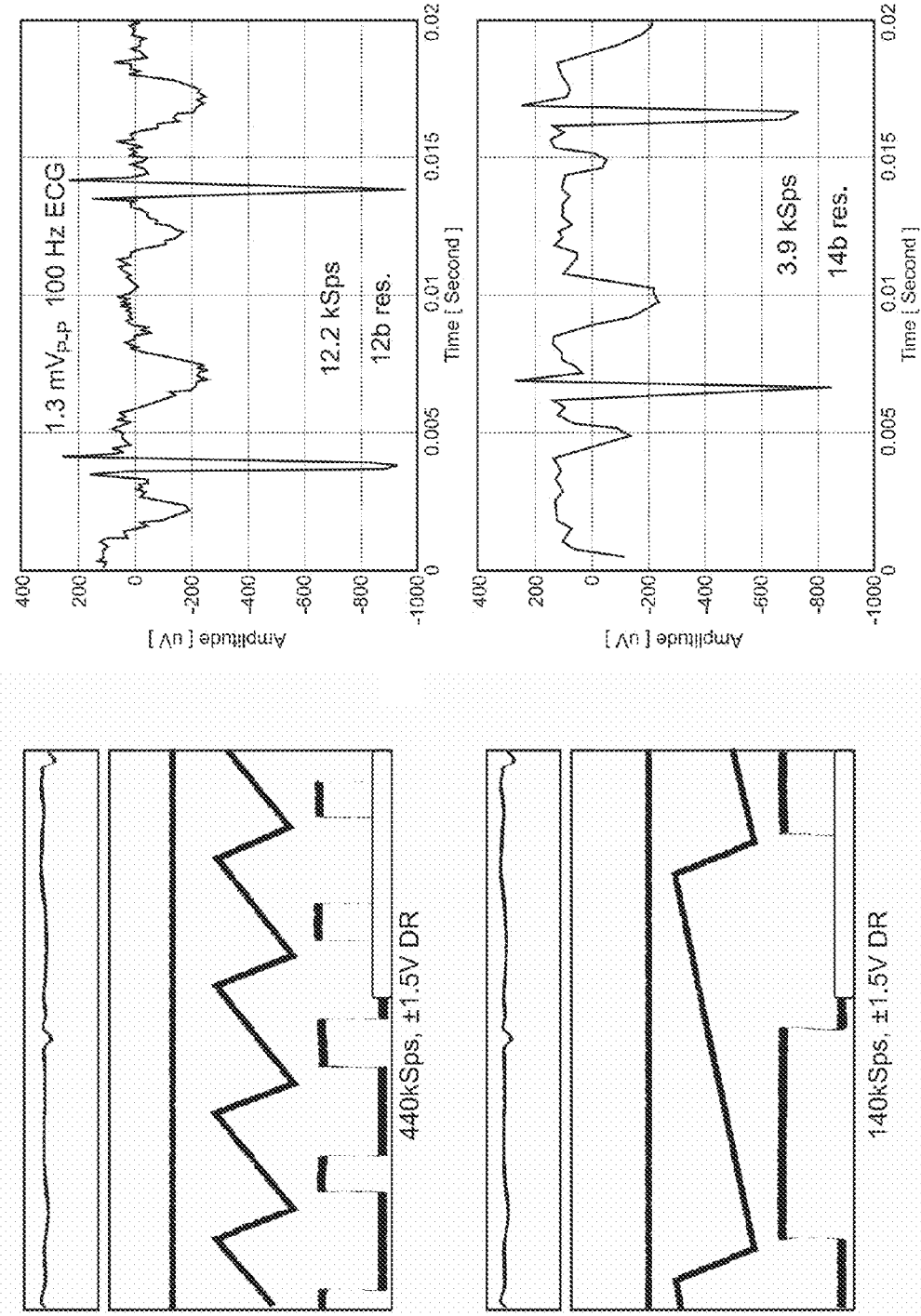
FIG. 12 illustrates graphical representations of waveforms depicting the effects of changing the sampling rate, which changes the time to digital conversion (TDC) resolution, in accordance with an exemplary embodiment of the present invention.

FIG. 12 illustrates graphical representations of waveforms depicting the effects of changing the sampling rate, which changes the time to digital converter resolution, in accordance with an exemplary embodiment of the present invention. These waveforms show the effect of changing the sampling rate, which also changes the TDC resolution. The upper waveform is approximately 1.3 mV and sampled at approximately 12.2 kSps. This creates a TDC resolution of 12 bits. The lower waveform is the same signal sampled at approximately 3.9 kSps. By lowering the triangular waveform frequency, the resolution is increased to 14 bits.

Figure 13:
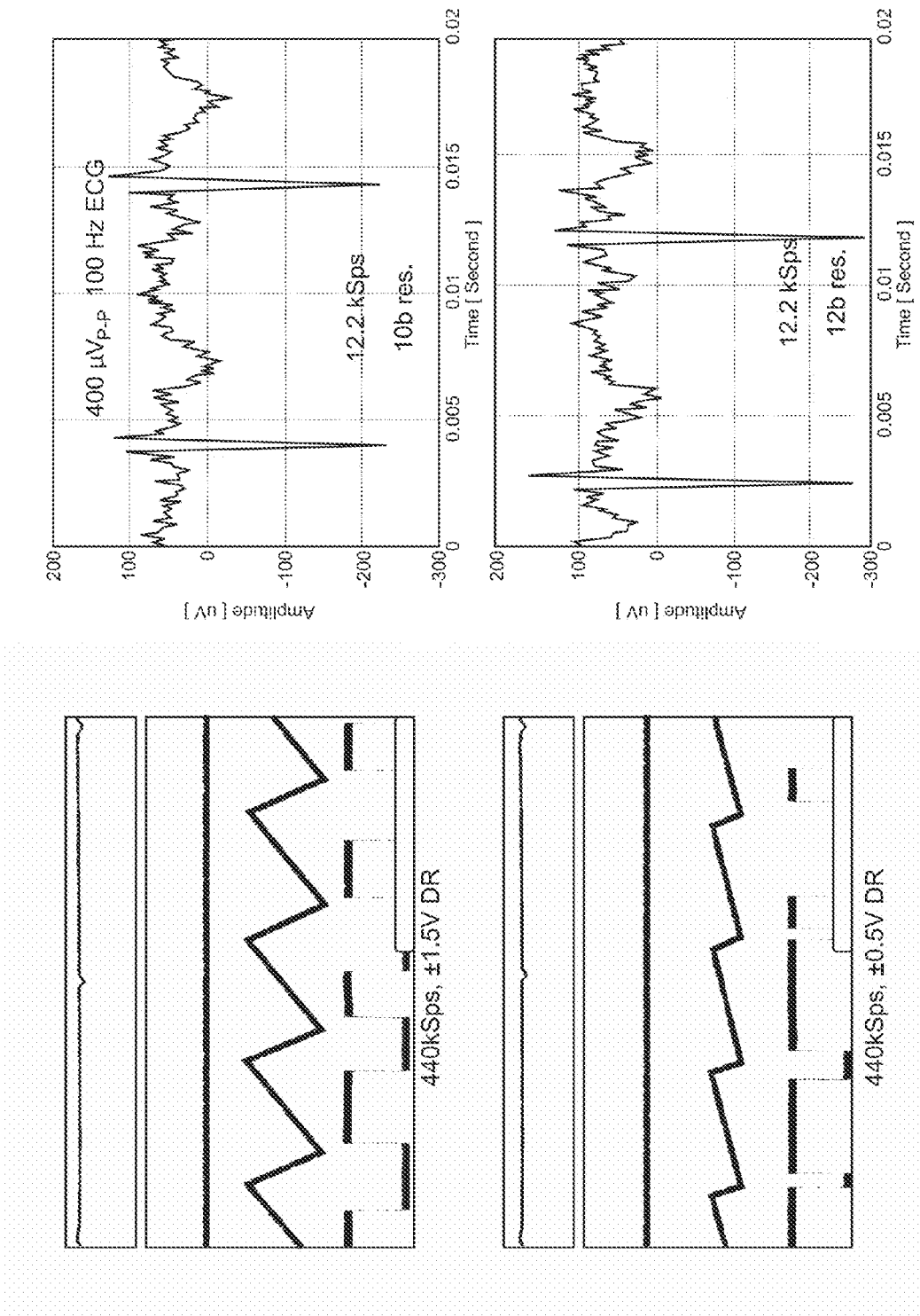
FIG. 13 illustrates graphical representations of amplitude of a triangular wave adjusted to the amplitude of an input signal to improve resolution, in accordance with an exemplary embodiment of the present invention.

FIG. 13 illustrates graphical representations of the amplitude of a triangular wave is adjusted to the amplitude of an input signal to improve resolution, in accordance with an exemplary embodiment of the present invention. These waveforms show the effect of changing the dynamic range. Here, the amplitude of the triangular wave is adjusted to the amplitude of the input signal to improve the resolution. In both waveforms depicted, the input signals are approximately 400 μV, and the sampling rates are approximately 12.2 kSps. By adjusting the TW amplitude to the input signal range, the lower waveform increases the resolution from 10 bits to 12 bits.

Figure 14:
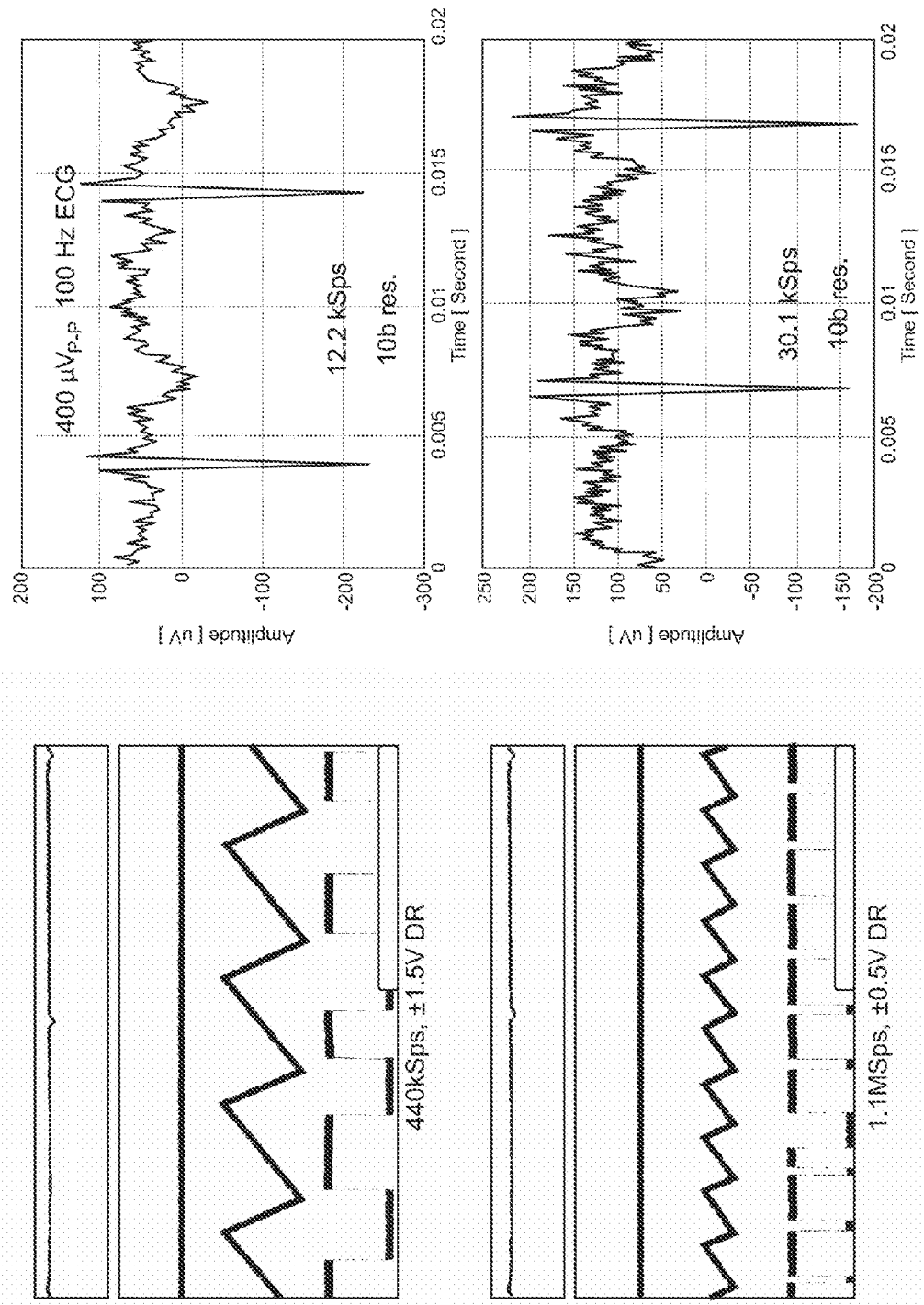
FIG. 14 illustrates graphical representations of an effect of increasing the sampling rate on reducing the system resolution, which has been compensated by adjusting the amplitude of the triangular wave, in accordance with an exemplary embodiment of the present invention.

FIG. 14 illustrates graphical representations of an effect of increasing the sampling rate on reducing resolution, in accordance with an exemplary embodiment of the present invention. The effect of increasing the sampling rate on reducing the resolution has been compensated by adjusting the dynamic range of the system.

Figure 15:
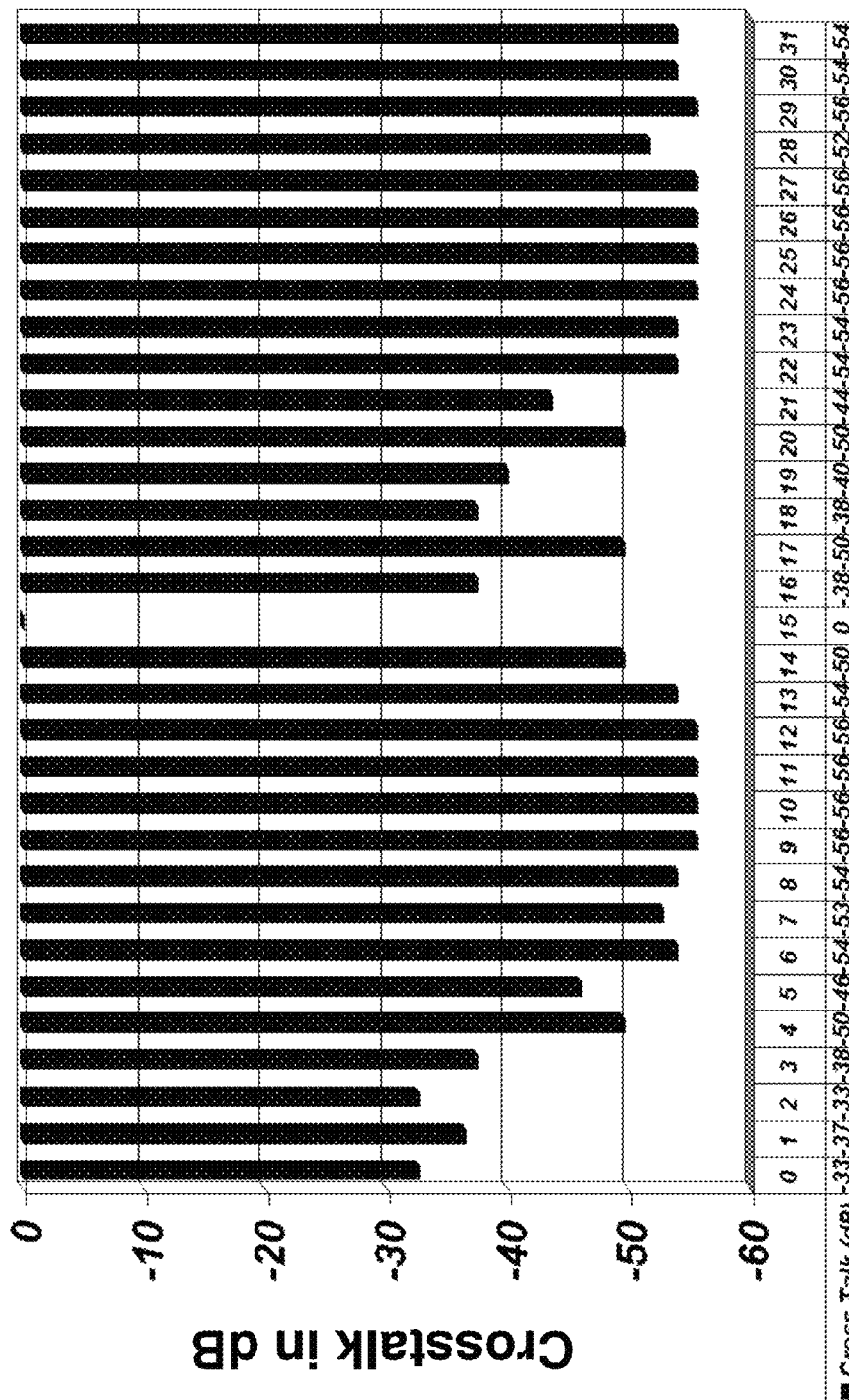
FIG. 15 illustrates a graphical representation of crosstalk among different channels from the low noise amplifiers to the processing block of the system in the computer, in accordance with an exemplary embodiment of the present invention.

FIG. 15 illustrates a graphical representation of crosstalk from low noise amplifiers to the processing system, in accordance with an exemplary embodiment of the present invention. For this measurement, one of the 32 channels was provided with a 1 kHz sine wave, and the remaining channels were grounded. Then the ratio between the amplitude of the signal received from every channel and the channel with sine wave was measured. The worst case crosstalk through the entire system was approximately −34 dB.

Figure 16:
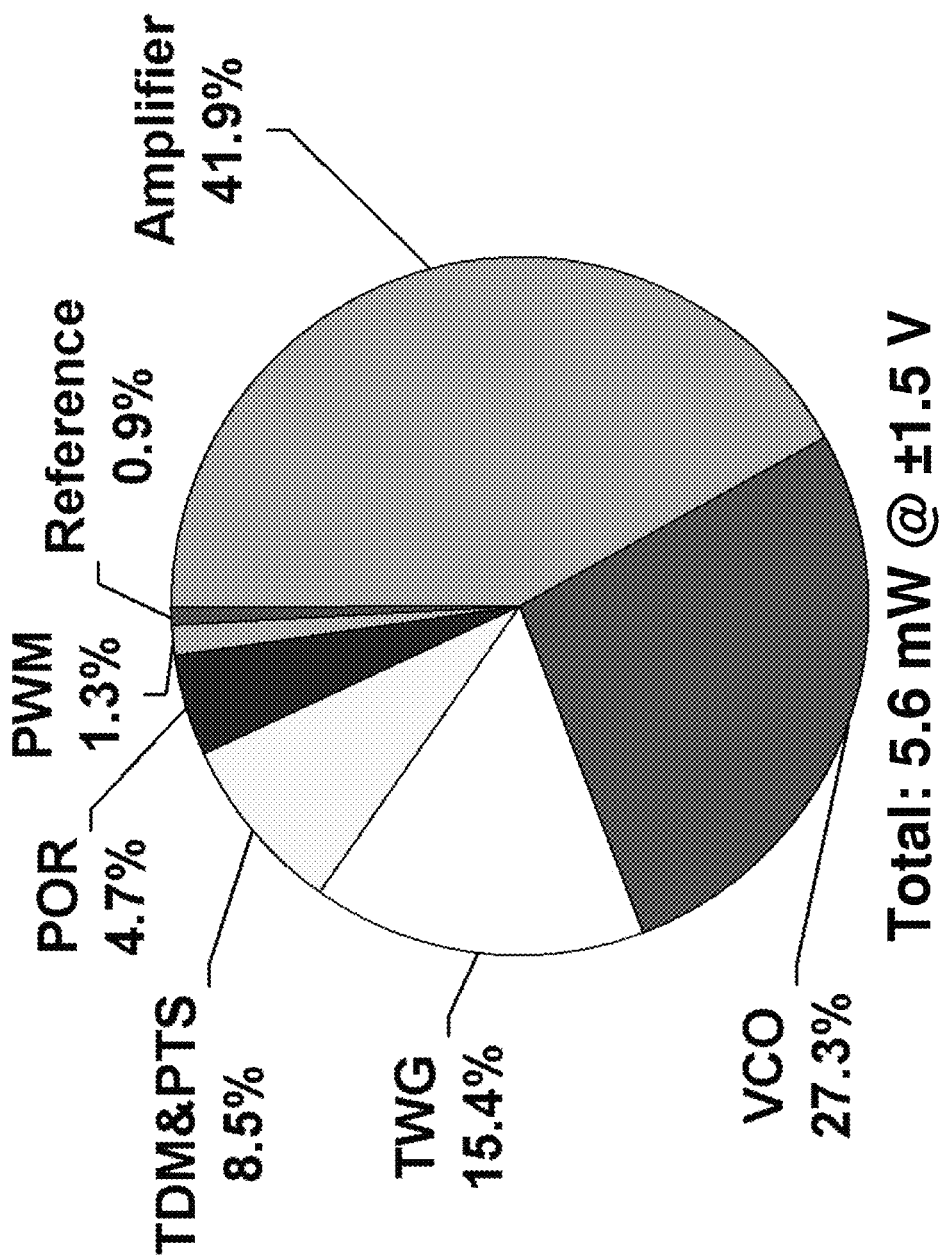
FIG. 16 illustrates a graphical representation of power consumption of the transmitter of the wireless neural recording system, in accordance with an exemplary embodiment of the present invention.

FIG. 16 illustrates a graphical representation of power consumption of the transmitter 200 of the wireless neural recording system 100, in accordance with an exemplary embodiment of the present invention. As illustrated, the power chart shows that the front-end amplifier 250 consumes most of the power, followed by the VCO 290 and the TWG 400. The estimated total power consumption of the transmitter 200 is approximately 5.6 mW at ±1.5V.

Figure 17:
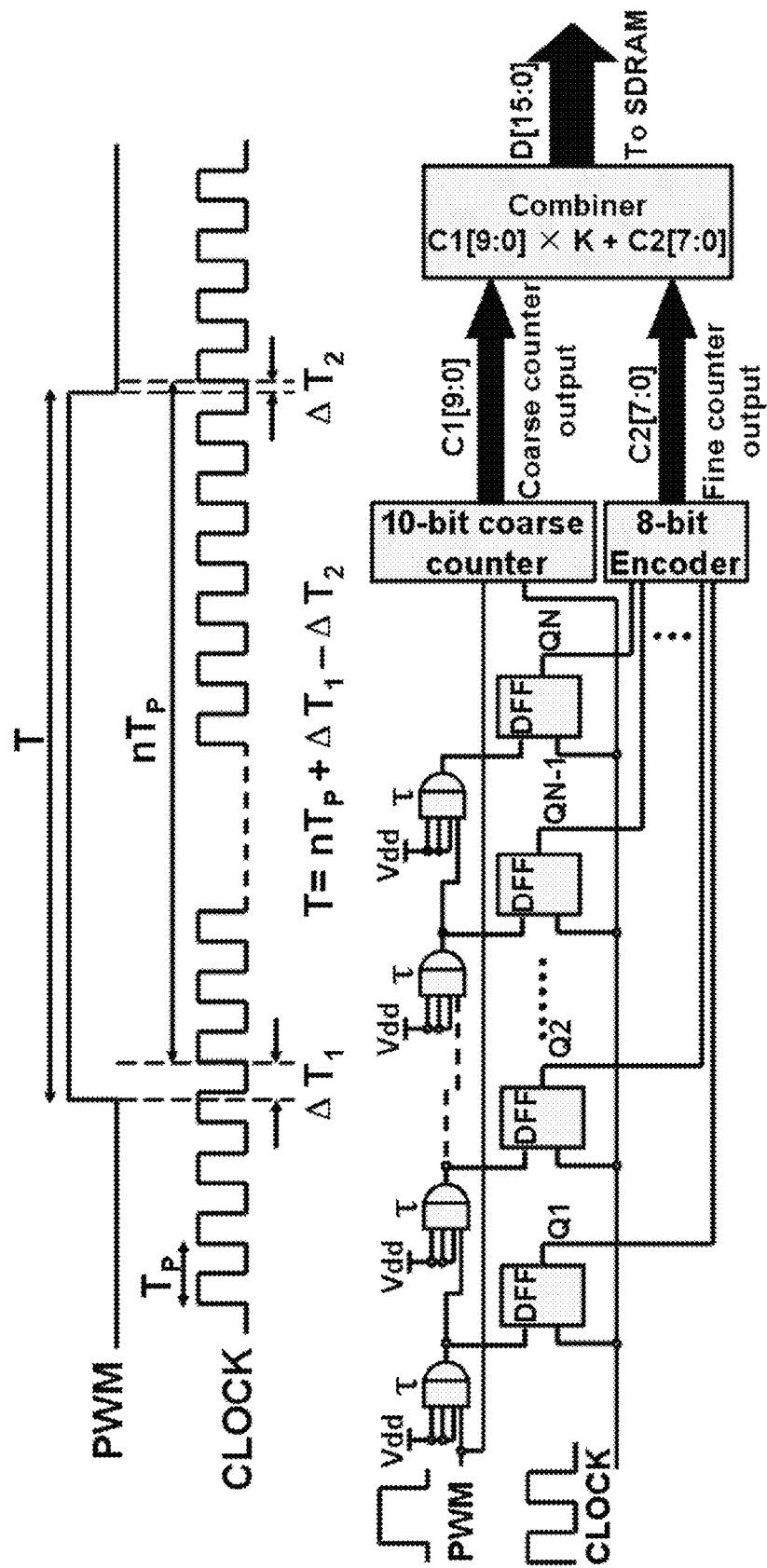
FIG. 17 illustrates a time to digital converter (TDC) of a receiver unit of FIG. 2B of the wireless neural recording system, in accordance with an exemplary embodiment of the present invention.

FIG. 17 illustrated a time to digital converter (TDC) of a receiver of the wireless neural recording system, in accordance with an exemplary embodiment of the present invention. The TDC includes a coarse counter using approximately 48 MHz FPGA main clock and including a fine counter that uses logic delay chain.

An evaluation of the wireless system can be explored by its potential sources of noise and inaccuracy. A goal of many embodiments of the present invention is to indicate the signal to noise ratio (SNR) of the signal arrived at the processing unit (e.g., the computer), which represents the noise in the entire system. Various sources of error in the reconstructed signal can be divided into those that are related to a) the implantable transmitter unit and b) the external receiver unit. Transmitter errors include errors in generating the triangular waveform, PWM comparator noise, offset, and hysteresis, and the VCO phase noise. On the receiver side, error is mostly due to the bandwidth limitation and internal noise, particularly at the RF front end of the receiver. Since the amplitude data is encoded in the pulse width, in this system the main purpose of the receiver is not to reconstruct the exact transmitted PWM waveform but to accurately measure the time intervals between every two successive transitions in the received FSK carrier frequency.

First, as the PWM block is illustrated in FIG. 5, the PWM noise includes both the TWG noise and the PWM comparator noise. As mentioned, a complementary current source/sink (CCSS) linearly charges/discharges a capacitor $C_S$ between $V_{high}$ and $V_{low}$. The resulting triangular wave is compared with $V_{in}$ and generates the PWM pulse width $$w = CV_{in}\left(\frac{1}{I_{Source}} + \frac{1}{I_{Sink}}\right). \tag{1}$$

The pulse width jitter can be expressed as $$\frac{dw}{T} = D\left(\frac{dC}{C} - \frac{I_{Sink}I_{Source}}{I_{Source}+I_{Sink}}\left(\frac{dI_{Source}}{I_{Source}^2}+\frac{dI_{Sink}}{I_{Sink}^2}\right)\right) + \frac{dV_{in}}{V_{high}-V_{low}}, \quad (2)$$

where T is the sampling period, dw is the changes in the PWM pulse width, and D=w/T is the PWM duty cycle. Variations in the TWG capacitor over time are often very small. In addition, $dV_{in}$ is the equivalent input referred noise of the comparator. Because the noise on $V_{high}$ and $V_{low}$ will also affect dw, comparator noises may need to be considered. The $dI_{Source}$ and $dI_{Sink}$ can be the noise contributions of the CCSS. Although the finite output impedance of the CCSS also contributes to dw, it mostly causes distortion, which can be compensated in calibration.

To calculate the power of the jitter, comparators are assumed to be identical with an input referred noise of $V_{n,comp}^2$ $$\frac{w_{n,PWM}^2}{T^2} = \left(\frac{DI_{Sink}I_{Source}}{I_{Source}+I_{Sink}}\right)^2\left(\frac{i_{n,Source}^2}{I_{Source}^4}+\frac{i_{n,Sink}^2}{I_{Sink}^4}\right)+3\left(\frac{V_{n,comp}}{V_{high}-V_{low}}\right)^2, \quad (3)$$

where $i_{n,Source}^2$ and $i_{n,Sink}^2$ are the current noise for the CCSS current source and sink, respectively.

Figure 18A:
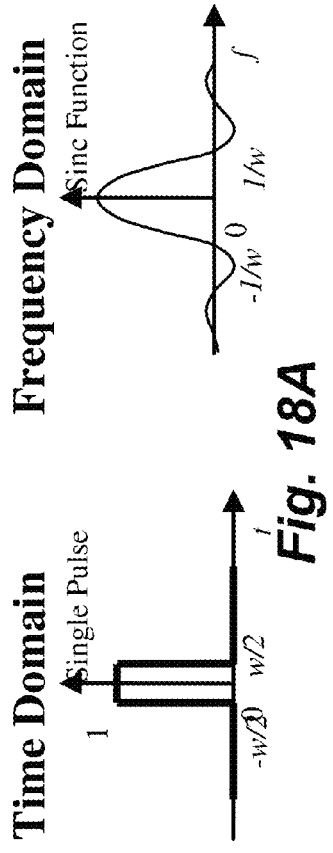
FIGS. 18A-18C illustrate graphical representations of a transmitter frequency shift keying-pulse width modulated-time division multiplexed (FSK-PWM-TDM) signal in both time (left) and frequency (right) domains, in accordance with an exemplary embodiment of the present invention.
Figure 18B:
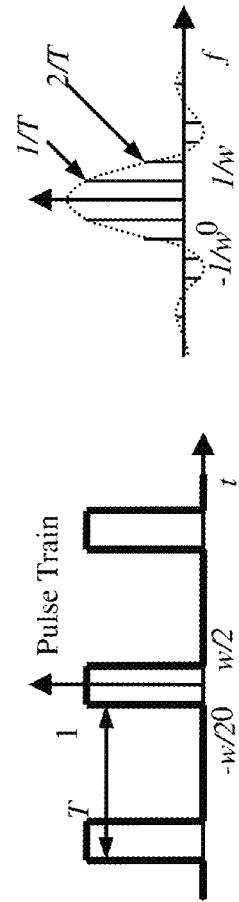
Figure 18C:
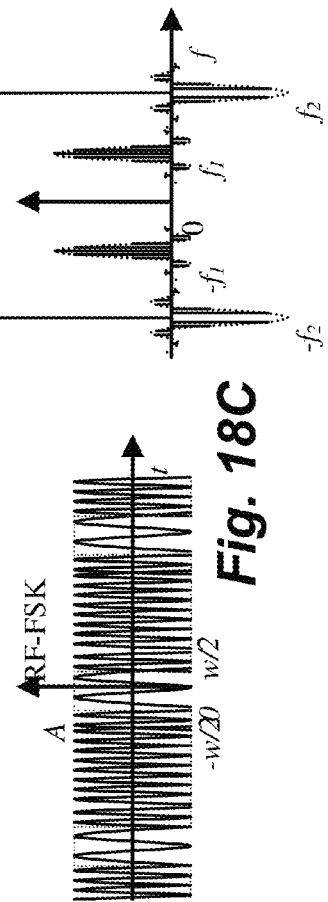

As for VCO noise, the VCO is the block that should be driven by the PWM comparator to create, in an exemplary embodiment, a FSK-PWM-TDM carrier signal (see FIGS. 18A-18B). In this process, the PWM spectrum can be shifted from baseband to FSK frequencies, $f_1$ and $f_2$. A single square pulse with width w can be described in time and frequency domains.

$$\Pi\left(\frac{t}{w}\right) = \begin{cases} 0, |t| > \frac{w}{2} \\ 1, |t| < \frac{w}{2} \\ \frac{1}{2}, |t| = \frac{w}{2} \end{cases}, \quad (4)$$

$$F\left[\Pi\left(\frac{t}{w}\right)\right] = \frac{\sin\pi fw}{\pi f}.$$

For a simple analysis, assume $V_{in}$ is constant and the PWM period is T. The analysis for more complicated PWM signals with variable pulse width can be found in the prior art [R. Guinee and C. Lyden, "A novel Fourier series time function for modeling and simulation of PWM," *IEEE Trans. on Circuits and Sys. I*, vol. 52, no. 11, pp. 2427-2435, November 2005.]. The PWM pulse train can be written as illustrated in FIG. 18B, $$PWM(t) = \sum_{n=-\infty}^{+\infty} \Pi\left(\frac{t-nT}{w}\right), \quad (5)$$

$$PWM(f) = \sum_{n=-\infty}^{+\infty} \frac{\sin\pi\frac{nw}{T}}{\pi\frac{n}{T}}\delta\left(f-\frac{n}{T}\right),$$

where $\delta(f)$ is the delta function. The FSK-PWM spectrum can then be found by shifting equation 5 to $\pm f_1$ and $\pm f_2$.

$$FSK-PWM(t) = \quad (6)$$

$$\sum_{n=-\infty}^{+\infty} \Pi\left(\frac{t-nT}{w}\right)A\cos2\pi f_1 t + \left(1 - \Pi\left(\frac{t-nT}{w}\right)\right)A\cos2\pi f_2 t$$

$$FSK-PWM(f) = \frac{A}{2}\sum_{n=-\infty}^{+\infty}\delta\left(f\pm f_1-\frac{n}{T}\right)\frac{\sin\pi\frac{nw}{T}}{\pi\frac{n}{T}} -$$

$$\frac{A}{2}\sum_{n=-\infty}^{+\infty}\delta\left(f\pm f_2-\frac{n}{T}\right)\frac{\sin\pi\frac{nw}{T}}{\pi\frac{n}{T}}+\frac{A}{2}\delta(f\pm f_2)$$

In the frequency domain, the VCO output will be the convolution of equation 6 and the VCO phase noise spectrum, $S_\Phi(f)$, at an offset frequency, f, away from the carrier, $f_{osc}$. After receiving, down converting, and filtering of the FSK-PWM-TDM, if the bandwidth limitation is ignored for the time being, the restored signal in the time domain will be the ideal PWM pulses in equation 5, shaped by the phase noise function $$PWM_{Rx}(t) = \sum_{n=-\infty}^{+\infty}\Pi\left(\frac{t-nT}{w}\right)F^{-1}[S_\Phi(f)]. \quad (7)$$

For white noise sources, frequency stability of the VCO is often characterized by the relative jitter, $$S_\Phi(f) \cong \frac{f_{osc}}{f^2}\left(\frac{\Delta\tau_{rms}}{T_{osc}}\right)^2, \quad (8)$$

where $\Delta\tau_{rms}$ is the rms jitter, $f_{osc}$ and $T_{osc}$ are VCO carrier frequency and period. Using equation 8, the result is:

$$\left(\frac{\Delta f_{rms}}{f_{osc}}\right)^2 = \left(\frac{\Delta\tau_{rms}}{T_{osc}}\right)^2 = S_\Phi(f)\frac{f^2}{f_{osc}}. \quad (9)$$

The VCO phase noise results in a frequency noise of $\Delta f_{rms}$, which after frequency demodulation turns into an rms voltage noise, $\Delta V_{rms}$. Due to the rising and falling slopes of the recovered PWM signal, $\Delta V_{rms}$ causes a pulse width error of $\Delta T_{VCO}$, which can be found from $$\frac{\Delta T_{VCO}}{T_{f/r}} = \frac{\Delta V_{rms}}{V_{pp}} = \frac{\Delta f_{rms}}{f_2-f_1}, \quad (10)$$

where $T_{f/r}$ is the sum of the rise and fall times and $V_{PP}$ is the peak to peak voltage of the recovered PWM signal. Using equations 9 and 10, the PWM duty cycle error is $$\Delta D = \frac{\Delta T_{VCO}}{T} = \frac{fT_{f/r}\sqrt{S_\Phi(f)f_{osc}}}{T(f_2-f_1)}, \quad (11)$$

where f is the offset frequency at which VCO phase noise has been measured. Therefore, increasing the FSK modulation index and reducing $T_{f/r}$ can help reducing the VCO error.

Gradual VCO drift does not affect the FSK-PWM signal, because it does not affect the pulse width. VCO settling time, however, is an important parameter determined by the VCO bandwidth and phase margin, which in turn depend on the VCO's tail current, LC tank quality factor, and loading (see FIG. 8).

As for external receiver errors, the receiver thermal noise, the local oscillator phase noise, and the receiver bandwidth limitation should be considered. Starting with the receiver thermal noise, the maximum noise power transfer occurs when there is impedance matching between successive blocks. This is usually the case in commercial devices because they are mostly designed for approximately 50Ω floating. Matching between the receiver antenna and front-end RF LNA results in transferred noise power of $$P_n = kT\Delta f, \tag{12}$$

where $\Delta f$ is the receiver RF front-end bandwidth. At room temperature, equation 12 in dBm becomes $$P_{n,dBm}[-174 + 10\log(\Delta f)]dBm \tag{13}$$

Every stage in FIG. 1 has a thermal noise characterized by its noise factor, F, and noise figure NF=10×log(F). If several stages with the gains of $G_1, G_2, \ldots, G_n$ and noise factors of $F_1, F_2, \ldots, F_n$ are connected in series, then $$F = F_1 + \frac{F_2 - 1}{G_1} + \frac{F_3 - 1}{G_1 G_2} + \ldots + \frac{F_n - 1}{G_1 G_2 \ldots G_n}. \tag{14}$$

If the first two stages have a high enough gain, considering the first 3 terms in equation 14 would be sufficient.

The thermal noise for a receiver with an approximately 50Ω input impedance that is connected to an antenna with approximately 50Ω radiation resistance is:

$$P_{n,Rx,dBm} = P_{n,dBm} + 10\log(F-1)[-174 + 10\log(\Delta f) + 10\log(F-1)]dBm. \tag{15}$$

If the input signal RF power ($P_{sig}$) is known, we can find the SNR for each stage. For PWM signal, the SNR is the reciprocal of pulse width duty cycle error.

$$SNR_{PWM} = \left(\frac{T}{\Delta w}\right)^2 = \frac{1}{\Delta D^2}. \tag{16}$$

Hence, the total receiver thermal noise contribution to the pulse width duty cycle error would be $$\Delta D = \sqrt{\frac{1}{SNR_{PWM}}} \tag{17}$$

$$= 10^{(P_{n,Rx,dBm} - P_{sig,Rx,dBm})/20}$$

$$\approx 10^{\left[-174 + 10\log(\Delta f) + 10\log\left(F_1 + \frac{F_2-1}{G_1} + \frac{F_3-1}{G_1 G_2} - 1\right) - P_{sig,Rx,dBm}\right]/20}.$$

As for the local oscillator (LO) phase noise, the amplified FSK-PWM signal can be down converted to IF-FSK-PWM by multiplication with a local oscillator ($f_{LO}$). The resulting signal will be similar to equation 6 when shifting the carrier frequencies from $f_1$ and $f_2$ to $f_1-f_{LO}$ and $f_2-f_{LO}$, respectively (see FIGS. 19A-19C), and the error analysis will be similar to that of the VCO. The commercial LO, however, often has a much lower phase noise compared to the transmitter VCO, and the LO contribution to pulse width jitter can be ignored.

Figure 19A:
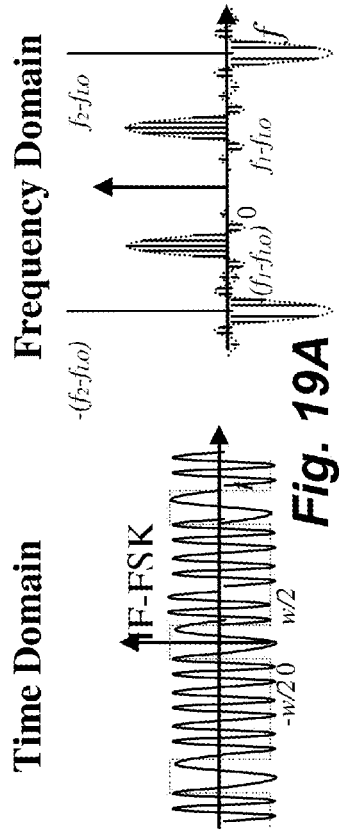
FIGS. 19A-19C illustrate graphical representations of a receiver pulse width modulated-time division multiplexed (PWM-TDM) signal in both time (left) and frequency (right) domains, in accordance with an exemplary embodiment of the present invention.
Figure 19B:
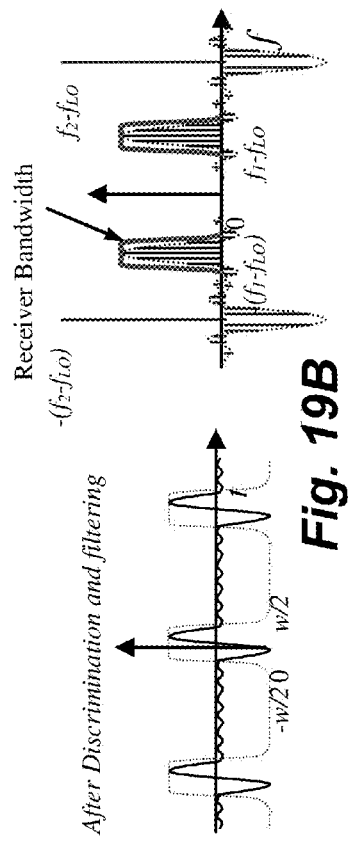
Figure 19C:
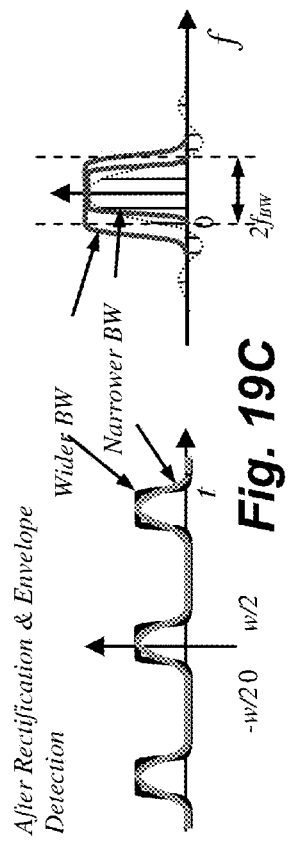

As for the receiver bandwidth (RBW) limitation, edges of the recovered PWM signal become rounded due to a RBW limitation, introducing pulse width error to the system. The analysis can be simplified by considering the receiver as an ideal low pass filter with cutoff frequency of $f_{BW}$, which limits the PWM spectrum to $-f_{BW} \sim f_{BW}$ range. FIGS. 19A-19C shows the received IF and baseband PWM signal in time and frequency domains. Mathematically, the complete PWM spectrum in equation 5 can be multiplied by the receiver low pass filter $$PWM_{Rx}(f) = \sum_{n=-\infty}^{+\infty} A \frac{\sin\pi\frac{nW}{T}}{\pi\frac{n}{T}} \frac{\delta\left(f \pm \frac{n}{T}\right)}{2} \Pi\left(\frac{f - f_{BW}}{2 f_{BW}}\right) \tag{18}$$

$$= \sum_{n=-M}^{+M} A \frac{\sin\pi nD}{\pi\frac{n}{T}} \frac{\delta\left(f \pm \frac{n}{T}\right)}{2}$$

where $f_{BW}T - 1 < M$ (integer) $\leq f_{BW}T$, and A is the amplitude of the recovered pulses. To find the pulse width error due to the RBW limitation, equation 18 returns back to time domain using inverse Fourier transform, $$PWM_{Rx}(t) = \sum_{n=-M}^{+M} A \frac{\sin\pi nD}{\pi\frac{n}{T}} \cos\frac{2\pi nt}{T}. \tag{19}$$

By setting a threshold at A/2, and solving $PWM_{Rx}(t) = A/2$ for t, the recovered pulse width, $w_{Rx} = 2t$, and duty cycle $D_{Rx} = w_{Rx}/T$ can be determined. It should be noted that if $M \to \infty$, i.e. unlimited RBW, then $2t = w$ and $D_{Rx} = D$. From equation 19, the result is $$\sum_{n=-M}^{+M} \frac{\sin\pi nD \cos\pi nD_{Rx}}{\pi\frac{n}{T}} = \frac{1}{2} \tag{20}$$

$$= \sum_{n=-\infty}^{+\infty} \frac{\sin\pi nD \cos\pi nD}{\pi\frac{n}{T}}.$$

Subtracting $$\sum_{n=-M}^{+M} \frac{\sin\pi nD \cos\pi nD}{\pi\frac{n}{T}}$$

from both sides yields $$\sum_{n=-M}^{+M} \frac{\sin\pi nD (\cos\pi nD_{Rx} - \cos\pi nD)}{\pi\frac{n}{T}} = \sum_{|n|>M} \frac{\sin\pi nD \cos\pi nD}{\pi\frac{n}{T}},$$

which simplifies to $$\sum_{n=-M}^{+M} \frac{\sin\pi nD\left(2\sin\pi n\frac{D_{Rx}+D}{2}\cdot\sin\pi n\frac{D_{Rx}-D}{2}\right)}{\pi\frac{n}{T}} = \sum_{|n|>M} \frac{\sin 2\pi nD}{2\pi\frac{n}{T}}. \quad (21)$$

Defining $D_{Rx}-D=\Delta D$, and assuming $\pi n\Delta D \ll 1$, where $n \le M$, then $$\sum_{n=-M}^{+M} (\sin\pi nD)^2 \Delta D = \sum_{n=-M}^{+M} \frac{1-\cos 2\pi nD}{2} \Delta D \quad (22)$$
$$= \sum_{|n|>M} \frac{\sin 2\pi nD}{2\pi n}.$$

Using equations 20, 21, and 22, the RBW duty cycle error can be found from $$\Delta D(M, D) = \frac{\sum_{|n|>M} \frac{\sin 2\pi nD}{2\pi n}}{\sum_{n=-M}^{+M} \frac{1-\cos 2\pi nD}{2}}. \quad (23)$$

Figures 20A, 20B:
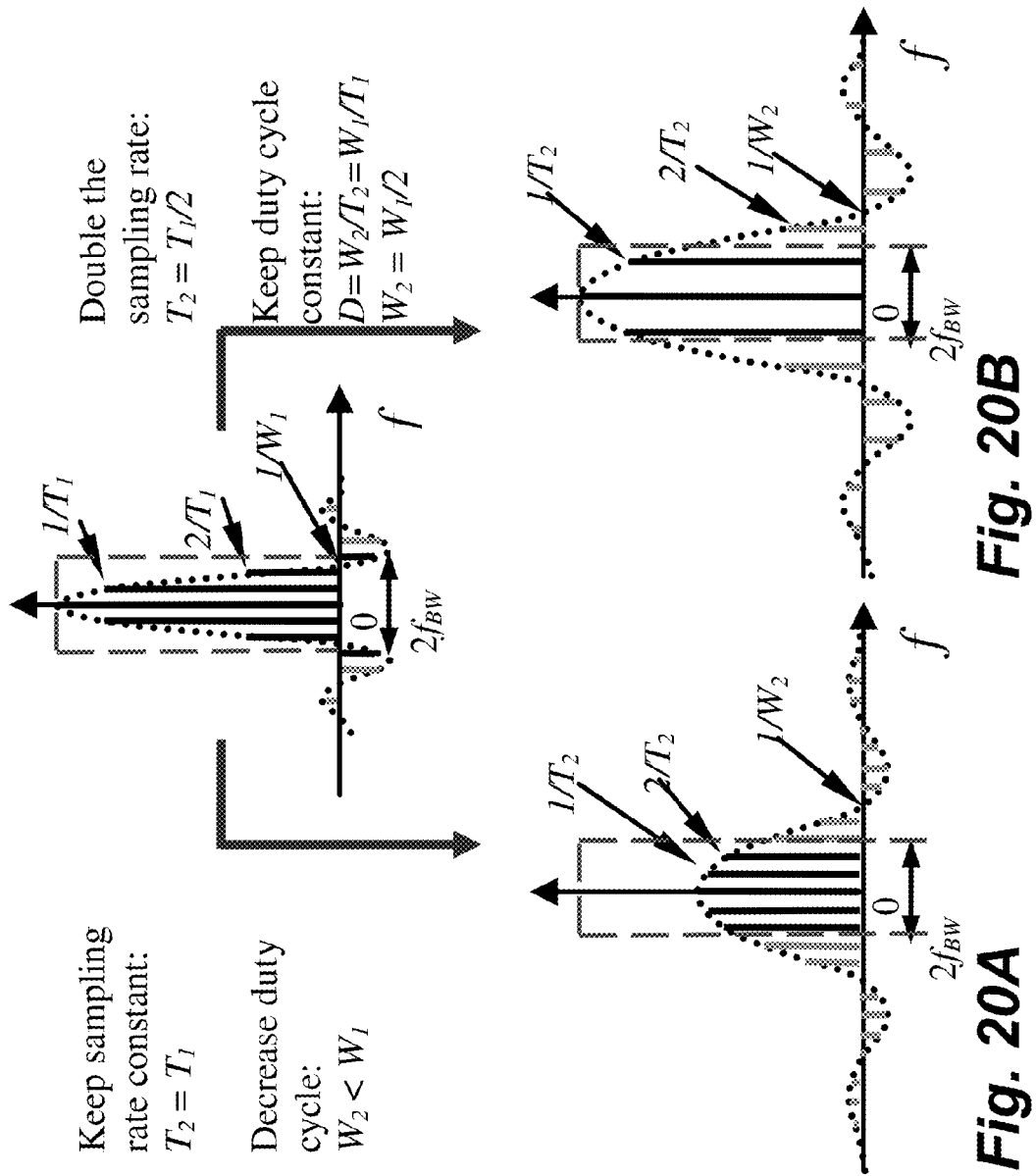
FIG. 20A illustrates a graphical representation of effects of receiver bandwidth limitation on the spectrum of the recovered pulse width modulated signal in a constant sampling frequency with a reduced pulse width modulated duty cycle, in accordance with an exemplary embodiment of the present invention.
FIG. 20B illustrates a graphical representation of effects of receiver bandwidth limitation on the spectrum of the recovered pulse width modulated signal in a constant pulse width modulated duty cycle with an increased sampling rate, in accordance with an exemplary embodiment of the present invention.

The numerator of equation 23 includes the even terms of the PWM Fourier series in equation 5 that are left outside of the RBW and decreases with increasing the RBW. The denominator of equation 23 increases with M, which is proportional to RBW. Hence, $\Delta D$ decreases with increasing RBW, and AD depends on D and consequently on T as shown in FIG. 20. For a fixed sampling period, T, if D decreases (i.e. $W_2<W_1$ in FIG. 20a), the PWM spectrum spreads further out along with a reduction in the amplitude of its in-band components. Therefore, if the RBW is fixed, more power will be outside of the RBW and AD increases. A similar situation can occur if $D\to 1$. Because in that case, the denominator of equation 23 becomes small, resulting in higher $\Delta D$. This makes sense because when $D\to 1$ the "low" pulses in PWM signal become quite narrow. Therefore, we need to limit $0<D<1$ from both ends.

Increasing the sampling rate without increasing the RBW can also have a detrimental effect on $\Delta D$ even if D is kept constant. This is demonstrated in FIG. 20B, where sampling rate is doubled ($T_2=T_1/2\to M_2=M_1/2$). This means that there will be more terms of the PWM spectrum outside RBW, which lead to a larger numerator in equation 23 and higher $\Delta D$.

Figures 21A, 21B:
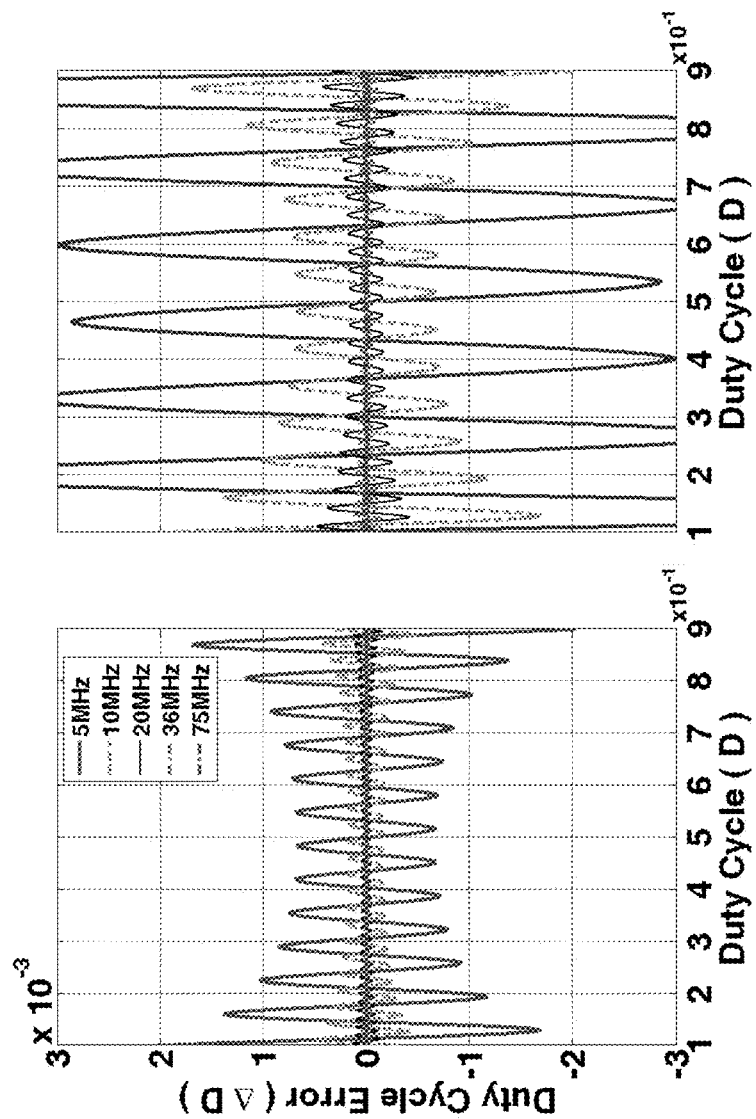
FIG. 21A illustrates a graphical representation of a theoretical pulse width modulated duty cycle error due to receiver bandwidth limits at approximately 5, 10, 20, 36, and 75 MHz for an approximate 320 kHz sampling rate, in accordance with an exemplary embodiment of the present invention.
FIG. 21B illustrates a graphical representation of a theoretical pulse width modulated duty cycle error due to receiver bandwidth limits at approximately 5, 10, 20, 36, and 75 MHz for an approximate 640 kHz sampling rate, in accordance with an exemplary embodiment of the present invention.
Figure 22:
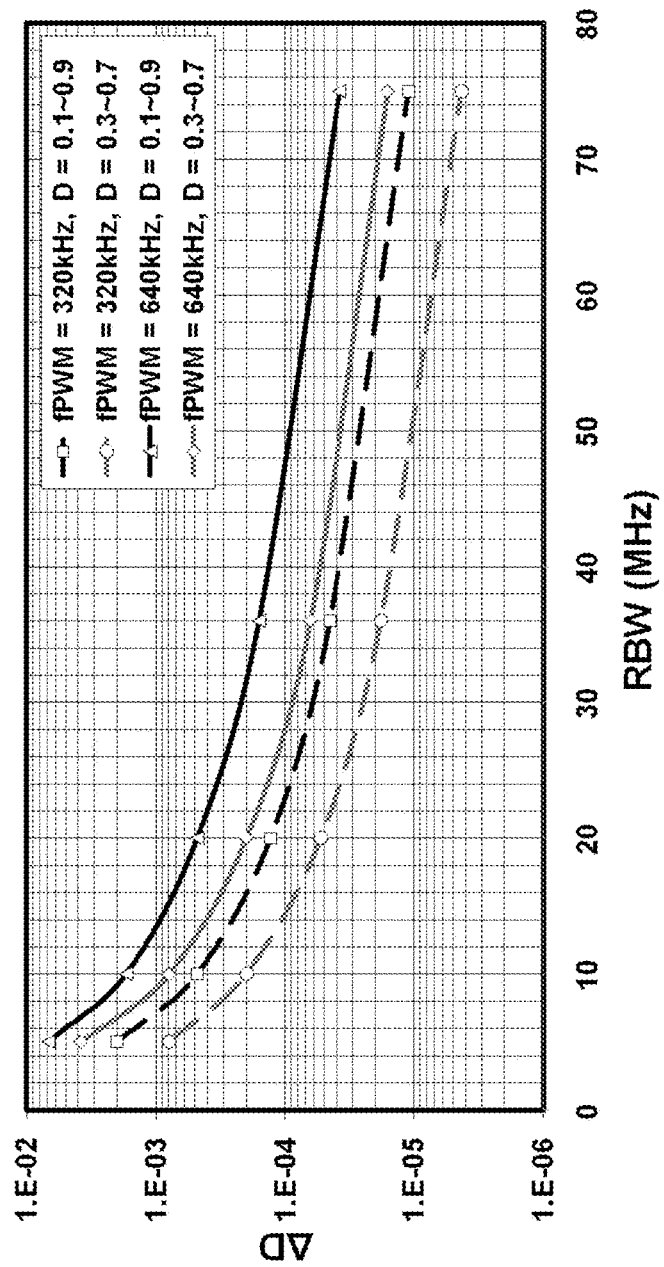
FIG. 22 illustrates a graphical representation of dependence of the pulse width modulated duty cycle error on sampling rate, PWM duty cycle, and receiver bandwidth, in accordance with an exemplary embodiment of the present invention.

In FIG. 21, a graphical representation of the plot of $\Delta D$ vs. D based on equation 23 for various RBWs from 5 to 75 MHz, and sampling rates of 320 and 640 kHz is illustrated. In order to reduce $\Delta D$, D has been limited to approximately 10 to 90%. FIG. 22 illustrates theoretical worst cases of $\Delta D$ variations with RBW and D for 16 channel and 32 channel PWM-TDM systems, sampled at approximately 20 kHz/ch. As illustrated, $\Delta D$, which can eventually define the overall resolution of the system in wireless PWM techniques, can be adjusted based on the number of active channels and the desired sampling rate per channel. Therefore, unlike digital approaches, depending on the application, characteristics of the biological signal and quality of the recording, the user can establish a tradeoff among the accuracy of the system, bandwidth per channel, and total number of active channels.

EXAMPLE

The various embodiments of the present invention are further illustrated by the following non-limiting example. A 32 channel ASIC was fabricated in the AMI 0.5-µm 3M2P standard CMOS process, and measured 3.3×3 mm². When recording channels are active, it consumes approximately 5.6 mW from approximately ±1.5 V supplies, as shown in FIG. 16.

The front-end amplifier first and second stages of the LNA block had a measured gain of approximately 40 dB and approximately 27.7/37.1 dB, respectively. The low-cutoff was continuously tunable in the approximately 0.1 Hz to 1 kHz range, while the high-cutoff was 4-bit programmable from approximately 0.7 to 10 kHz. This topology provides approximately 1% THD at approximately 17.4 mV input. The fully differential design leads to approximately 65 dB power supply rejection ratio (PSRR) and approximately 139 dB common-mode rejection ratio (CMRR) with approximately 3.9 $\mu V_{rms}$ input referred noise in approximately 10 Hz to 10 kHz range. Because of capacitive coupling, the amplifiers are robust against input baseline variations and random first stage offset. The crosstalk for adjacent channels was smaller than approximately −42 dB.

The CCSS has a maximum $I_{Source}$ and $I_{Sink}$ of approximately 34.6 and 123.3 PA, and provides voltage compliance from approximately −1.4 V to 1.4 V. Measurements indicated that the TWG operates as expected and the triangular wave can vary from approximately 0 to ±1.4 V. For the maximum output swing (approximately 2.8 $V_{p-p}$), the system sampling rate could be adjusted in 225 steps from 58 kHz to 680 kHz using $DP_{0-3}$ and $DN_{0-3}$ digital inputs.

The functionality of the entire system was bench-top tested using three function generators creating an approximate 30 Hz cardiac signal (reference 1000 in FIG. 10), approximately 80 Hz triangular waveform and an approximately 100 Hz sine wave, which were attenuated and voltage divided to generate four equally spaced amplitude levels below approximately one mV. Eight out of 12 signals were given to three channels each (a total of 24 inputs), and the other four signals were given to two channels each (the rest of eight inputs). These signals were amplified and filtered by the LNA block at approximately 67.7 dB and approximately 0.1 Hz to 10 kHz, respectively. The TWG output signal was adjusted at approximately ±1.4 V and approximately 640 kHz, which indicates the overall sampling rate of the system (reference 1010 in FIG. 10). The PWM block compared the 32 LNA outputs and four monitoring signals with the TWG output, and the MUX organized the resulting PWM samples into frames of 36 pulses. The PTS was set to mask the TWG falling ramp in the resulting TDM-PWM signal. This signal drove the on-chip MOS varactor of the hybrid LC-VCO, running at approximately 898/926 MHz in the FSK mode. An approximately 1.1 nH off-chip surface mount inductor was used for the VCO with reasonable dimensions of approximately 1.85×1.37× 1.19 mm³ and Q=46 at 900 MHz (e.g., 0604HQ-1N1XJL, CoilCraft, Cary, Ill.).

The transmitted FSK-TDM-PWM carrier was picked up at approximately one meter from the system by the receiver. The receiver amplified and down converted the FSK signal to approximately 42/70 MHz IF-TDM-PWM (reference 1020 in FIG. 10), and further rectified and filtered to a baseband TDM-PWM signal with approximately 18 MHz bandwidth. It was then translated to TTL levels (reference 1030 in FIG. 10), and sent to the FPGA-based TDC for digitization. The 16-bit digitized samples were buffered in SDRAM and sent to a processing system, e.g., a PC, through its USB port. On the PC, a Visual C++ GUI was operated to record, demultiplex, and demonstrate the received waveforms in real-time, which are shown in FIG. 11. In this experiment, each of these waveforms has been sampled at 640 kHz/36=17.8 kHz. This rate, however, can be simply changed by programming the TWG through $I_{Source}$, $I_{Sink}$, $V_{low}$ and $V_{high}$ adjustable parameters.

In an exemplary embodiment, Table I shows a summary of the specifications of the transmitter for the 32 channel system on an ASIC.

TABLE I

SUMMARY OF TRANSMITTER ASIC SPECIFICATIONS

| Number of channels | 32 recording + 4 monitoring |
| --- | --- |
| LNA gain (dB) | 67.7 and 77.1 |
| LNA CMRR and PSRR (dB) | 139 and 65 |
| LNA input referred noise (µVrms) | 3.9 |
| LNA low cutoff (Hz) | 0.01~1000 (continuous) |
| LNA high cutoff (kHz) | 0.7~10 (16 levels) |
| Sampling rate (kHz) | 58~680 |
| FSK carrier frequency (MHz) | 898/926 |
| Entire system input referred noise (µVrms) | 4.9 @ 1 m distance |
| Total power dissipation (mW) | 5.6 |
| Power supply (V) | ±1.5 |
| Technology | 0.5-µm 3M2P Std. CMOS |
| Die size (mm) | 3.3 × 3 |

The input referred noise of the entire 32 channel system was measured by grounding most of the channels and conducting fast Fourier analysis on the recorded signals from three channels (e.g., Ch. 4, Ch. 14 and Ch. 24) in approximately 1.28 s at an approximately one meter distance. The input referred noise spectrum density had a noise corner at approximately 10 kHz. Integration of these curves from approximately 1 Hz to 10 kHz resulted in an input referred noise of approximately 4.90, 4.95, and 4.93 $\mu V_{rms}$ for the measured channels, respectively. Noise contributed at each major stage was also analyzed and measured. In an exemplary embodiment, Table II shows a summary of noise contributions by each major block.

TABLE II

SUMMARY OF NOISE CONTRIBUTIONS*

| | Transmitter | | | Receiver | |
| --- | --- | --- | --- | --- | --- |
| Circuit | TWG | Comparator | VCO | Bandwidth limitation | LNA/Mixer/IF Stage |
| Pulse width Noise (ns) | 1.3 | 1.05 | 0.024 | 0.97 | 2.13 |
| Equivalent SNR (dB) | 61.5 | 63.5 | 96.4 | 64.2 | 57.3 |
| ENOB** | 10.2 | 10.5 | 16.0 | 10.7 | 9.5 |
| Entire System Resolution: | | | 8.8 | | |

*At approximately 640 kHz sampling rate, approximately 18 MHz receiver bandwidth and approximately 10% to 90% PWM duty cycle range;
**Equivalent number of bits.

This example presents a highly flexible 32 channel wireless implantable neural recording system based on time division multiplexing of pulse width modulated signals. The substrate noise was suppressed using a novel TWG block that eliminates the on-chip high frequency clock. Measurement results indicate that the system is fully functional and can simultaneously record 32+4 channels wirelessly at 640 kSample/s in an approximately one meter distance, with more than 8 bits of resolution. This is equivalent to a bandwidth of 5.12 Mb/s throughout the system.

Furthermore, the various embodiments of the present invention are further illustrated by the following non-limiting example. For example, in order to experimentally evaluate the performance of the wireless PWM technique on the system, the measurement setup illustrated in FIG. 23 was used.

As mentioned, the plurality-channel prototype ASIC can be fabricated in the AMI 0.5-µm standard CMOS process and wire bonded on a PGA 132-pin package. $V_{high}$, $V_{low}$, $I_{Source}$, and $I_{Sink}$ of the PWM (see FIG. 5) were adjusted for a total sampling rate of $f_{PWM}$ approximately 640 kHz or 20 kHz per channel. The transmitter chip can be battery powered at approximately ±1.5 V, consuming approximately 5.6 mW, and the VCO was tuned to operate at 880/915 MHz when receiving a rail to rail PWM signal. On the receiver side, vector signal analyzer (e.g., Agilent 89600 VXI series) can be used with tunable bandwidth from approximately 5 to 36 MHz in addition to the wideband receiver with 75 MHz bandwidth. The down converted IF-FSK-PWM signal was digitized at approximately 4 GSps using an oscilloscope (e.g., Agilent MSO6104A) and the digitized data was further processed offline in a PC.

To further explore the effects of various system parameters on the wireless PWM performance, a realistic MATLAB-Simulink model was constructed including the blocks shown in FIGS. 2A and 2B.

Figure 24A:
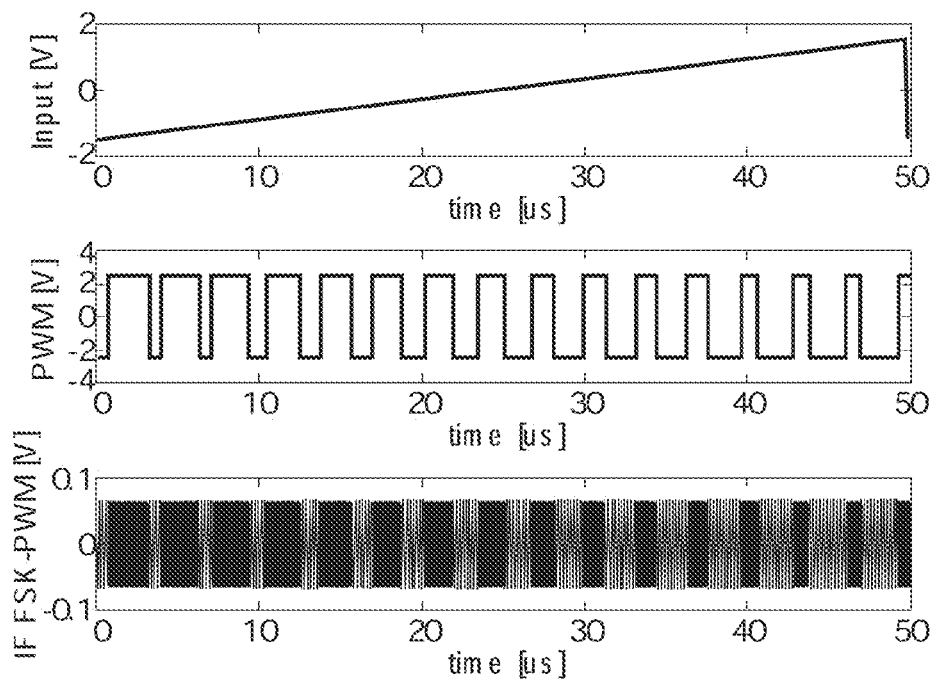
FIG. 24A illustrates a graphical representation of simulated ramp input and pulse width modulated-time division multiplexed (PWM-TDM) signal on a transmitter, and an intermediate frequency-frequency shifting keying-pulse width modulated (IF-FSK-PWM) signal on the receiver, in accordance with an exemplary embodiment of the present invention.
Figure 24B:
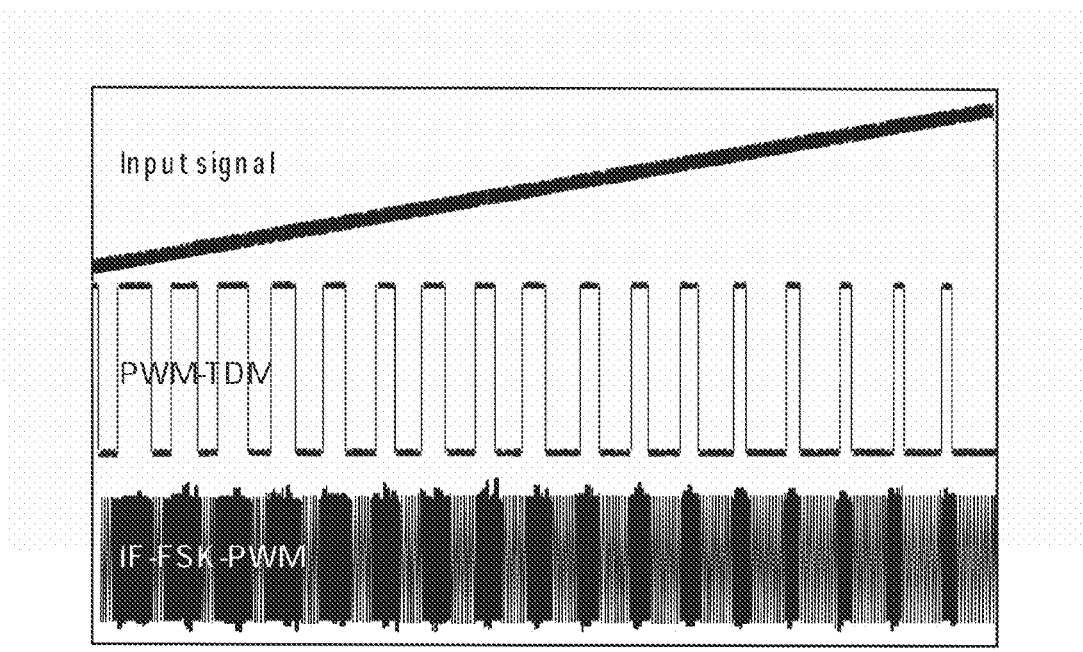
FIG. 24B illustrates a graphical representation of measured ramp input and PWM-TDM) signal on a transmitter, and an IF-FSK-PWM signal on the receiver, in accordance with an exemplary embodiment of the present invention.

FIGS. 24A-24B compare sample simulated versus measured waveforms when a ramp was applied to LNA inputs (e.g., 16 or 32 of them). In this experiment, $f_{LO}$ was tuned to approximately 952 MHz, and after down-conversion, the IF-FSK-PWM signal was centered on approximately 37 and 72 MHz (FIG. 19A). The approximate 37 MHz signal was located at the center of the receiver pass-band and receiver preserved most of its power, while the approximate 72 MHz signal was located outside and was attenuated by the IF filters (FIG. 19B). This signal can be easily envelope detected and sharpened by passing through a comparator to recover the PWM-TDM.

Figure 25A:
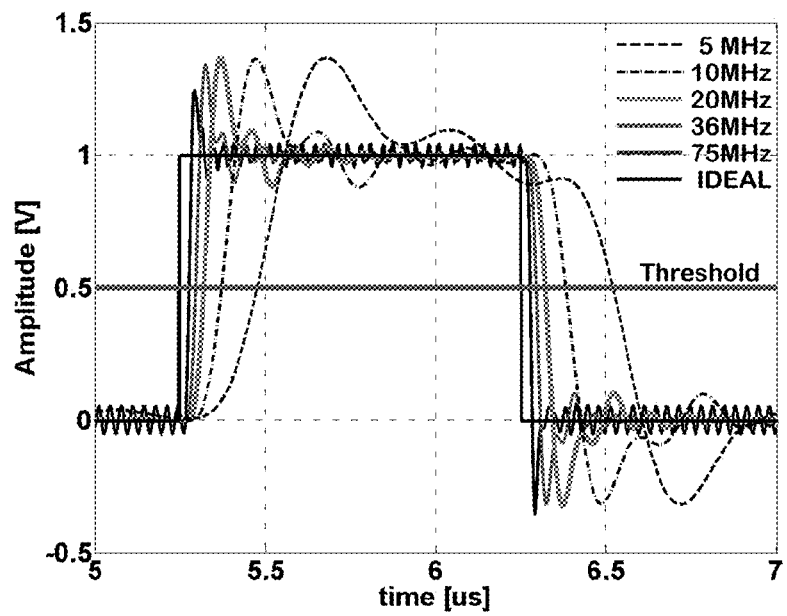
FIG. 25A illustrates a graphical representation of simulated variations in the recovered pulse width modulated waveform due to receiver bandwidth, in accordance with an exemplary embodiment of the present invention.

FIG. 25A shows simulated samples of recovered PWM pulses when changing the RBW from 5 to 75 MHz.

Figure 25B:
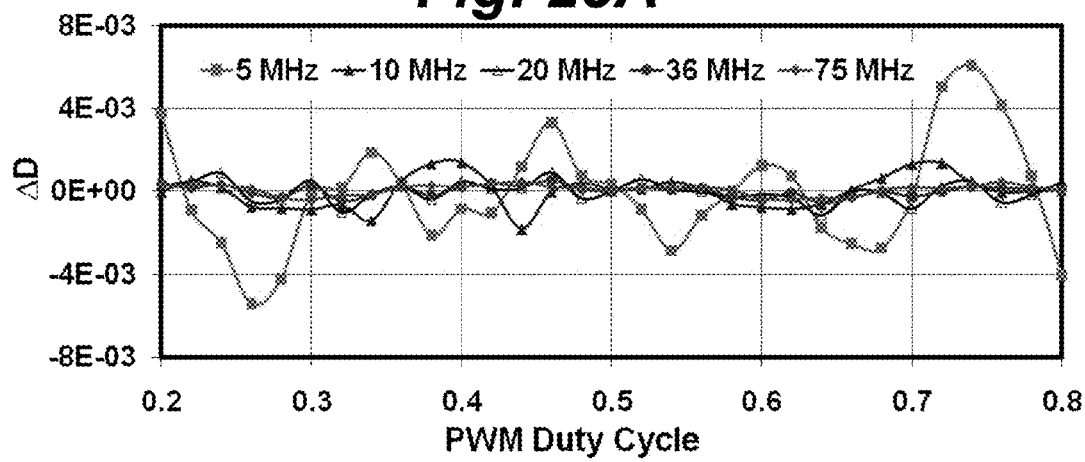
FIG. 25B illustrates a graphical representation of simulated pulse width modulated duty cycle error versus pulse width modulated duty cycle for different receiver bandwidths, in accordance with an exemplary embodiment of the present invention.

In FIG. 25B, the simulated results of duty cycle error from the 320 kHz MATLAB-Simulink model when RBW=5, 10, 20, 36, and 75 MHz and 0.2<D<0.8 are depicted. According to these curves, which closely resemble theoretical outcomes shown in FIGS. 21A-21B, with RBW=75 MHz, the PWM technique can achieve $\Delta D < 10^{-4}$.

Figure 23:
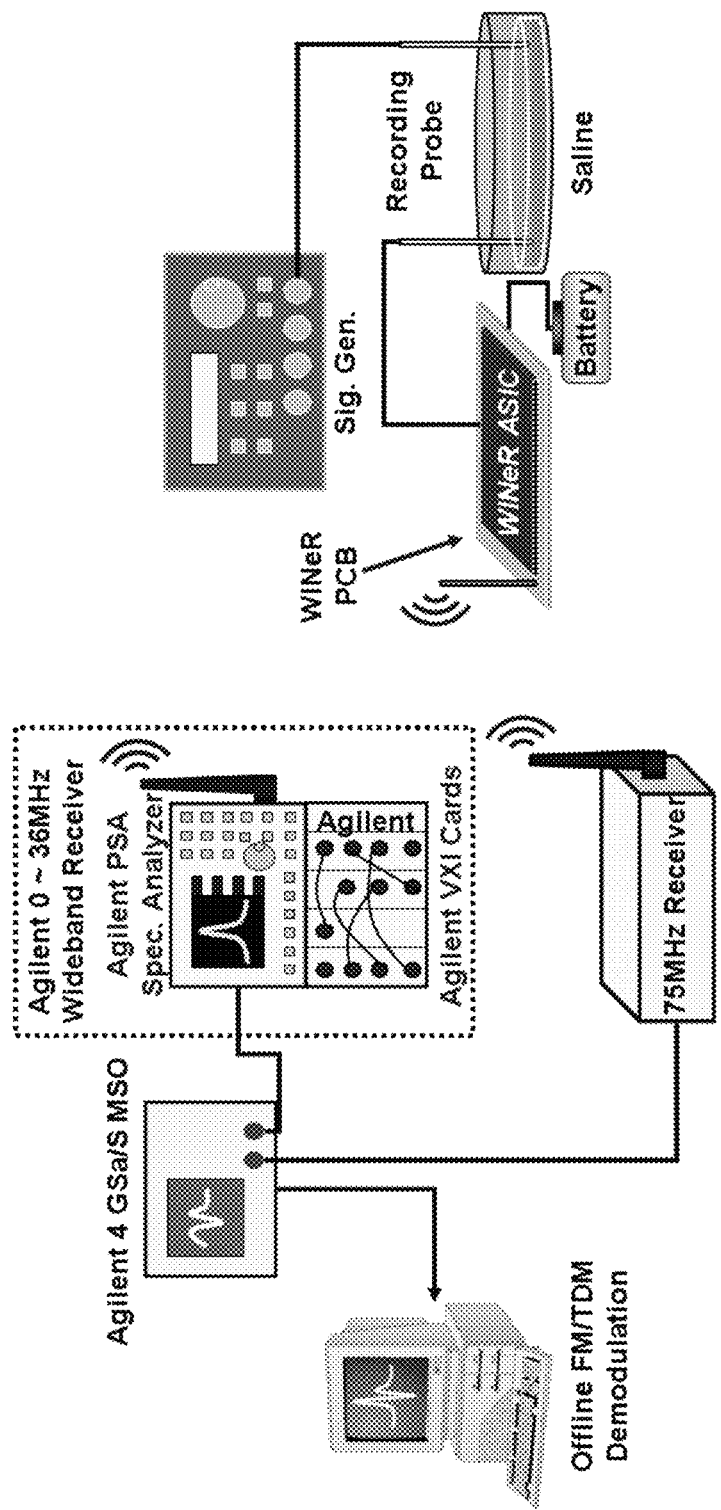
FIG. 23 illustrates a block diagram for an experimental setup for the wireless pulse width modulated technique using the transmitter of FIG. 2A, and wideband receivers of FIG. 2B from 5 to 75 MHz, in accordance with an exemplary embodiment of the present invention.

Using the setup in FIG. 23, the following wireless PWM performance measures were experimentally evaluated.

First, the comparator error was examined. The PWM comparator error was evaluated by applying a DC voltage and a rail-to-rail sawtooth waveform from a precision function generator (e.g., Agilent 33250A) with approximately 0.1% of peak linearity to the comparator inputs. The ideal pulse width when the sawtooth is greater than the DC voltage, and the actual output pulse width were compared for DC values swept from approximately −1.4 to 1.4 V in approximately 0.1 V steps. The rms value for $\Delta D$ due to comparator error was found to be less than $7 \times 10^{4}$.

Second, the TWG error was examined. According to equation 3, when $V_{high}$ and $V_{low}$ are constant, the TWG jitter is mainly due to the thermal noise of the CCSS and comparators. The TWG output was sampled at approximately 2.5 GHz, then subtracted from a straight line with the same slope (ideal TWG waveform), and calculated the rms noise. The current noise is related to the voltage noise by a factor of C/T. Once the current noise is known, it can be used in equation 3 along with the comparator noise. Measurements showed that the rms $\Delta D$ from TWG was less than $10^{-3}$.

Third, the VCO error was examined. Measurements showed that the VCO ($f_{osc} \cong 900$ MHz) has a phase noise of $S_\Phi(10$ kHz$)=-88.17$ dBc/Hz. At sampling rate of $f_{PWM}=320$ kHz and RBW=36 MHz, $T_{f/r}=74$ ns for the recovered PWM. Plugging these numbers in equation 11 results in $\Delta D \cong 10^{-5}$, which is far less than the other sources of error. Further, simulation and measurements showed that the VCO settling time is in the nanosecond range and it can be neglected with respect to T. Therefore, unlike high data rate digital wireless links, the VCO and LO on the transmitter and receiver units, respectively, do not have a dominant effect on the system accuracy.

Fourth, the receiver thermal noise was examined. The receiver noise figure is usually determined by the RF front-end LNA stages. The entire receiver SNR was expected to be very close to the SNR at the RF LNA output. Measurements at d=1 m between the receiver and transmitter at the LNA output resulted in $P_{sig,Rx}=-15.7$ dBm and $P_{n,Rx}=-73$ dBm. Substituting these values in equation 17 yields $\Delta D=1.4 \times 10^{-3}$. Even though this $\Delta D$ is not dominant in these measurement conditions, if the receiver SNR decreases as a result of increasing d or a strong interference, it has the potential to become the dominant source of noise and inaccuracy in the system. Proper matching between the receiver antenna and LNA input is also a crucial factor in improving the receiver sensitivity.

Figure 26:
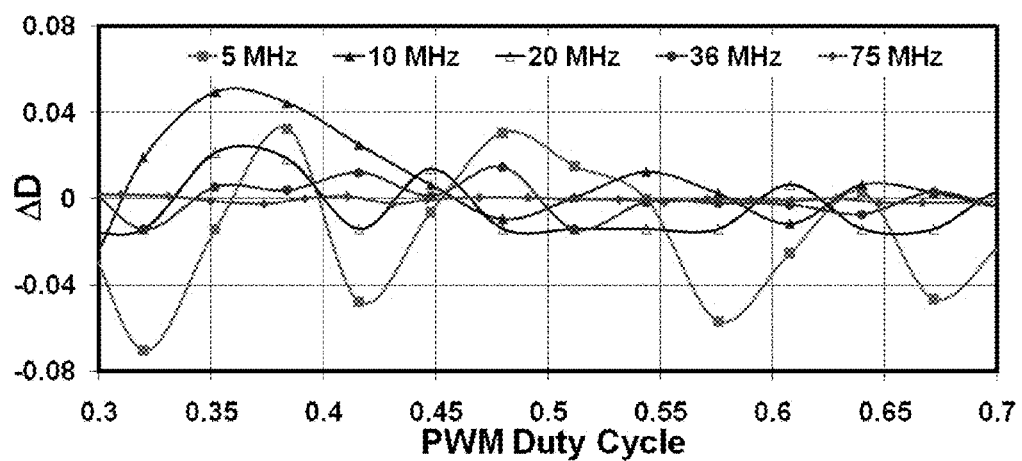
FIG. 26 illustrates a graphical representation of measured wireless pulse width modulated duty cycle error versus pulse width modulated duty cycle for different receiver bandwidth at an approximate 320 kHz sampling rate, in accordance with an exemplary embodiment of the present invention.

Fifth, the receiver bandwidth (RBW) limitation error was examined. For RBWs of approximately 5, 10, 20, 36, and 75 MHz we directly compared the widths of the transmitted and received pulses, while changing the PWM duty cycle from approximately 30% to 70%. FIG. 26 shows the measured $\Delta D$ vs. D for T=3.125 μs (320 kHz). As shown, the RBW is one of the most effective parameters in defining the wireless PWM resolution, and it can dominate other sources of error if it is not wide enough. For the system operating with the custom designed receiver (75 MHz), the worst case $\Delta D$ was approximately $2.4 \times 10^{-3}$ at D=29%, which is roughly the equivalent of $-\ln_2(2.4 \times 10^{-3})=8.7$ bits of resolution. Considering the other sources of error discussed earlier, one can conclude that the system can acquire 20 k-sample/sec/channel from 32 channels plus the four monitoring signals with at least 8.4 bits of resolution. Table III summarizes the measured $\Delta D$ contribution from different sources of error across the entire system.

TABLE III

SUMMARY OF CALCULATED DUTY CYCLE ERROR CONTRIBUTIONS FROM MEASURED PARAMETERS IN THE SYSTEM*

| | System | | | | |
|---|---|---|---|---|---|
| | | | | Receiver | |
| | Transmitter | | | RBW | |
| Block | TWG | Comparator | VCO | limitation | Receiver noise |
| $\Delta D$ | $10^{-3}$ | $7 \times 10^{-4}$ | $10^{-5}$ | $2.4 \times 10^{-3}$ | $1.4 \times 10^{-3}$ |
| Equivalent SNR | 60 dB | 63.1 dB | 100 dB | 52.4 dB | 57.3 dB |
| Equivalent NOB | 10.0 | 10.5 | 16.6 | 8.7 | 9.5 |
| System Resolution | | | | 8.4 bits | |

*$f_{PWM}$ = 320 kHz, $f_1/f_2$ = 915/880 MHz, 0.3 < D < 0.7, RBW = 75 MHz

Due to the fact that the majority of neuroscientists prefer to have access to the entire recorded neural signals across the wireless link as a seamless substitute to their hardwired data acquisition setups, the main alternative to our proposed TDM-PWM based architecture is the conventional digitization of the acquired neural signals before wireless transmission. In a 32+4 channel system, the ADC should take approximately 640 kS/s and produce approximately 5.12 Mbps of raw data, which has to be delivered across the wireless link. The advantages of the ATC system outweigh the advantages of the conventional ADC system.

1) ADC vs. ATC:

Both approaches need the multiplexer and S/H. Hence the comparison narrows further down to the ADC architecture of choice vs. FIG. 5, which is similar to the front-end of a single-slope ADC, in terms of speed, complexity, and power consumption. There are few ADC architectures as simple as FIG. 5, which can offer the necessary performance. Moreover, the ATC method does not need any additional clock signal, which can be a potential source of substrate noise and interference for the on-chip LNAs.

2) Handling of the Information Before Transmission:

As mentioned above and illustrated in FIG. 2A, the TDM-PWM signal directly drives the VCO. In an ADC-based architecture, on the other hand, digitized raw data has to be serialized, encoded, packetized, and combined with preamble and error detection bits. Even though these are routine tasks, the required digital circuitry can occupy a considerable chip area particularly in processes with large feature length, which are more suitable for low noise analog circuit blocks.

3) Fidelity of the Wireless Link:

Low power wireless links such as Bluetooth 2.0 can offer data rates close to 2.56 Mbps by relying on accurate time base generators that are crystal based. Crystals, however, cannot be integrated and occupy a large volume off chip. Transferring serial data at Mbps range with free-running VCOs does not seem to be feasible, and any effort in stabilizing the VCO frequency by using a phase-locked loop (PLL), for example, significantly increases the power consumption in the transmitter unit. On the other hand, the FSK-PWM-TDM signal has similar characteristics to digital FSK in being resistant to noise and interference. However, it does not need synchronization on a bit by bit basis. The VCO phase noise does not limit the system resolution, and its gradual drift can be compensated by tracking capability of the receiver.

Embodiments of the present invention transfer the digital blocks and their associated area/power consumption outside of the body by dividing the ADC process into ATC on the transmitter unit and TDC on the receiver unit.

Using a plurality channel wireless implantable neural recording system prototype, an effective architecture is presented for simultaneously acquiring wideband neural signals from a large number of sites. The system operates based on pulse width modulation of time division multiplexed samples (PWM-TDM), which can reduce the complexity, size, and power consumption of the implantable transmitter at the cost of adding to the complexity of the receiver without compromising the accuracy, robustness, or bandwidth of the entire system. It also provides the user with a high level of flexibility over the system resolution, sampling rate, and dynamic range.

One aspect of the present invention is to provide a system for transmitting bioelectrical signals. The system includes an implantable bioelectrical sensor for receiving at least one bioelectrical signal; an analog-to-time converter for converting the received bioelectrical signal from an analog domain to a time domain signal; and a radio frequency (RF) modulator for transmitting the time domain signal. The analog-to-time converter and the RF modulator are implantable in a living being.

In an exemplary embodiment, the system consumes no more than approximately 6 mW at approximately ±1.5V. Further, the implantable bioelectrical sensor includes an electrode for receiving at least one neural signal. The analog-to-time converter and the RF modulator are implantable in a brain of an animal or human. The surface area of the system is less than approximately 10 mm by 10 mm or smaller, e.g., 3 mm by 3 mm. The analog-to-time converter includes a low noise amplifier having built-in bandpass filtering characteristics to amplify and filter the received bioelectrical signal. The RF modulator is adapted to transmit a frequency shift keying signal. The received bioelectrical signal has a frequency range of approximately 0.1 Hz to 10 kHz. In addition, the analog-to-time converter includes a waveform generator for providing a consistent triangular waveform having a predetermined shape and amplitude. The system can increase the temperature of the living being by less than two degrees Centigrade.

Another aspect of the present invention relates to a method of monitoring one or more bioelectrical signals. The method comprises receiving the bioelectrical signals using an analog bioelectrical sensor implanted in a living being; converting the analog bioelectrical signals from an analog domain to a time domain signal; and wirelessly transmitting the time domain signal.

The method may further comprise modulating the time domain signal for transmission. In addition, the method may further comprise receiving receiving the wirelessly transmitted time domain signal and converting the received time domain signal to a digital domain signal for processing by a processing system. In an exemplary embodiment, receiving the bioelectrials signals includes a frequency range of approximately 0.1 Hz to 10 kHz.

Yet another aspect of the present invention relates to a system for recording neural signals of a brain. The system comprises a plurality of implanted electrode sensors placed in juxtaposition to one or more neural circuits for receiving at least one neural signal; a signal converter for converting the received neural signals to a asynchronous signal; and a radio frequency (RF) modulator for transmitting the asynchronous signal, wherein the signal converter and the RF modulator implantable in a living being.

In an exemplary embodiment, the system has a power consumption of less than approximately 6 milliwatts at approximately ±1.5V. In addition, the signal converter and the RF modulator are implantable in a brain of an animal or human. Furthermore, the system includes a surface area of less than 10 mm by 10 mm, or smaller, e.g., 3 mm by 3 mm.

In an exemplary embodiment, the signal converter includes a low noise amplifier system comprising a plurality of low noise amplifiers, each of the low noise amplifiers in communication with at least one of the plurality of implanted electrode sensors, each low noise amplifier for amplifying and filtering at least one received neural signal; a pulse width modulator system comprising a plurality of comparators, the pulse width modulator system converting an amplitude of the received amplified and filtered neural signals to a pulse width sample, the number of the plurality of comparators of the pulse width modulator system is at least greater than or equal to the number of the plurality of low noise amplifiers of the low noise amplifier system; a programmable triangular waveform system feeding a predetermined frequency and amplituded triangular waveform to the pulse width modulator system; a time division multiplexer for arranging the plurality of pulse width samples in a synchronous orientation; a masking system for limiting the pulse width modulated-time division multiplexed signal to either rising or falling ramps of a triangular wave by masking an opposing side for further synchronizing the pulse width modulated pulses at their rising or falling edges; and a voltage controlled oscillator for receiving the trimmed PWM-TDM signal from the masking system to output the asynchronous signal. Moreover, the receiver includes a asynchronous to digital converter for converting the received wirelessly transmitted signal of the transmitter system to a digital signal. The receiver further includes a processing system for processing the digital signal for interpretation and recording purposes. The system can be embedded within an enclosure, which is adapted to be embedded in a living being. The system can have a temperature range of less than three degree Centigrade.

While exemplary embodiments of the invention have been disclosed many modifications, additions, and deletions can be made therein without departing from the spirit and scope of the invention and its equivalents, as set forth in the following claims. In addition, the quantities of various features of embodiments of the present invention are provided for illustrated embodiments and are exemplary. The scope of the various embodiments of the present invention should not be limited to the above discussed embodiments or quantity values, and should only be defined by the following claims and all applicable equivalents.

What is claimed is:

1. A system for recording neural signals of a brain, the system comprising:
   a plurality of implantable electrode sensors placed in juxtaposition to one or more neural circuits for receiving at least one neural signal;
   an analog-to-time signal converter for converting the received neural signals to an asynchronous pulse-width-modulated signal, the analog-to-time signal converter comprising a low-noise amplifier configured to receive the neural signals and a comparator, wherein the comparator comprises a first input that receives the output of the low-noise amplifier and a second input that receives the output of a triangular waveform generator programmed with a predetermined frequency and directly compares the output of the triangular waveform generator to the output of the low-noise amplifier to generate the asynchronous pulse-width-modulated signal; and
   a radio frequency (RF) modulator for transmitting the asynchronous signal,
   the signal converter and the RF modulator designed to be implanted in a living being.

2. The system of claim 1, the system having a power consumption of less than approximately 6 milliwatts at approximately ±1.5V, and the system increasing the temperature of the living being by less than approximately 2 degrees Centigrade.

3. The system of claim 1, the signal converter and the RF modulator implantable in a brain of an animal or human.

4. The system of claim 1, the system comprising a surface area of less than approximately 10 mm by 10 mm.

5. A system for recording neural signals of a nervous system, the system comprising:
   a plurality of implantable electrode sensors placed in juxtaposition to one or more neural circuits for receiving at least one neural signal;
   a signal converter for converting the received neural signals to an asynchronous signal, and
   a radio frequency (RF) modulator for transmitting the asynchronous signal,
   the signal converter and the RF modulator designed to be implanted in a living being, the signal converter comprising:
- a low noise amplifier system comprising a plurality of low noise amplifiers, each of the low noise amplifiers in communication with at least one of the plurality of implanted electrode sensors, each low noise amplifier for amplifying and filtering at least one received neural signal;
- a pulse width modulator system comprising a plurality of comparators, wherein each comparator comprises a first input that receives the output of the low-noise amplifier and a second input that receives the output of a triangular waveform system, the pulse width modulator system converting an amplitude of the received amplified and filtered neural signals to a pulse width sample, the number of the plurality of comparators of the pulse width modulator system is at least greater than or equal to the number of the plurality of low noise amplifiers of the low noise amplifier system;
- a programmable triangular waveform system feeding a predetermined frequency and amplitude triangular waveform to the pulse width modulator system;
a time division multiplexer for receiving the plurality of pulse width samples and arranging the plurality of pulse width samples in a synchronous orientation;
- a masking system for trimming the pulse width modulated-time division multiplexed (PWM-TDM) signal to either rising or falling ramps of a triangular waveform by masking an opposing side for further synchronizing the pulse width modulated pulses at their rising or falling edges; and
- a voltage controlled oscillator for receiving the trimmed PWM-TDM signal from the masking system to output the asynchronous signal.

6. The system of claim 5, further comprising a receiver comprising a asynchronous to digital converter for converting the received wirelessly transmitted signal of the transmitter system to a digital signal, the receiver comprising a processing system for processing the digital signal for recording and interpretation.

7. The system of claim 1, the system embedded within an enclosure, the enclosure adapted to be embedded in a living being.

8. The system to claim 5, further comprising a receiver comprising:
- an RF demodulator for receiving the asynchronous signal transmitted by the RF modulator; and
- a time-to-digital signal converter for converting the received asynchronous signal from time events to a digital signal.

9. The system of claim 8, wherein the receiver comprises:
- a low noise amplifier system for amplifying and filtering the received asynchronous signal;
- a mixer for down converting the amplified and filtered received signal to an intermediate frequency band; and
- a rectifying and filtering system for rectifying and low-pass filtering the down-converted signal to recover a baseband PWM-TDM signal, wherein the time-to-digital converter is configured to receive the baseband PWM-TDM signal.

* * * * *